United States Patent
Shimizu et al.

(10) Patent No.: US 8,618,319 B2
(45) Date of Patent: Dec. 31, 2013

(54) METAL COMPLEX AND METHOD FOR PRODUCING α-OLEFIN POLYMER AND METHOD FOR PRODUCING α-OLEFIN/(METH)ACRYLATE COPOLYMER USING THE SAME

(75) Inventors: Fumihiko Shimizu, Kanagawa (JP); Shixuan Xin, Kanagawa (JP); Akio Tanna, Kanagawa (JP); Shiho Goromaru, Kanagawa (JP); Koushi Matsubara, Kanagawa (JP)

(73) Assignees: Japan Polypropylene Corporation, Tokyo (JP); Japan Polyethylene Corporation, Tokyo (JP)

( * ) Notice: Subject to any disclaimer, the term of this patent is extended or adjusted under 35 U.S.C. 154(b) by 329 days.

(21) Appl. No.: 13/126,360

(22) PCT Filed: Apr. 27, 2009

(86) PCT No.: PCT/JP2009/058263
§ 371 (c)(1),
(2), (4) Date: Apr. 27, 2011

(87) PCT Pub. No.: WO2010/050256
PCT Pub. Date: May 6, 2010

(65) Prior Publication Data
US 2011/0213110 A1 Sep. 1, 2011

(30) Foreign Application Priority Data
Oct. 30, 2008 (JP) .................................. 2008-280388

(51) Int. Cl.
C07F 15/00 (2006.01)
C07F 15/04 (2006.01)
C08F 4/26 (2006.01)
C08F 4/70 (2006.01)

(52) U.S. Cl.
USPC ........... 556/138; 556/136; 526/172; 526/171; 526/169; 526/169.1; 526/161; 526/170; 526/160; 526/348; 526/329; 526/328; 526/328.5

(58) Field of Classification Search
USPC .................. 556/136, 138; 526/172, 319, 328, 526/328.5, 329.7, 169.1
See application file for complete search history.

(56) References Cited

U.S. PATENT DOCUMENTS

| 4,698,403 | A | 10/1987 | Klabunde |
| 5,714,556 | A * | 2/1998 | Johnson et al. .............. 526/135 |
| 6,103,920 | A | 8/2000 | Johnson et al. |
| 2007/0049712 | A1 | 3/2007 | Allen et al. |

FOREIGN PATENT DOCUMENTS

| CN | 1133659 C | 1/2004 |
| JP | 64 14217 | 1/1989 |
| JP | 2005-179322 A * | 7/2005 ................ C07F 9/50 |
| JP | 11 508635 | 7/2009 |

OTHER PUBLICATIONS

Kurosawa et al., Bull.Chem. Soc. Jpn., 1987, 60, 3563-3567.*
Dunbar et al., Inorg. Chim. Acta, 1995, 240, 527-534.*
Heinicke, J.; Peulecke, N.; Kindermann, M.K.; Jones, P.G. Z. Anorg. Allg. Chem. 2005, 631, 67-73.*
Dunbar, K.R.; Sun, J.-S.; Quillevere, A. Inorg. Chem. 1994, 33, 3598-3601.*
Sun, S.-J.; Uzelmeier, C.E.; Ward, D.L.; Dunbar, K.R. Polyhedron 1998, 17(11-12), 2049-2063.*
Ma, J-F et al., "Reactions of Palladium Complex of N, N-Dimethylbenzylamine With Aromatic Phosphines Bearing the Methoxy Groups at the 2, 6-Positions", Journal of Organometallic Chemistry, vol. 616, No. (1-2), pp. 149-156 (2000).
Kurosawa, H. et al., "1-3-ῆ -Allylpalladium (II) and Platinum (II) Complexes Containing Tris(2,6-Dimethoxyphenyl) Phosphine Ligand", Bulletin of the Chemical Society of Japan, vol. 60, No. 10, pp. 3563-3567, (1987).
Heinicke, J. et al., "A Novel Access to Phenylnickel-Phosphinophenolate Trimethylphosphine Complexes As Single Component Oligo- or Polymerization Catalysts", Zeitschrift Fuer Anorganische Und Allgemeine Chemie, vol. 631, No. 1, pp. 67-73, (2005).
Mecking, S. et al., "Mechanistic Studies of the Palladium-Catalyzed Copolymerization of Ethylene and α-Olefins With Methyl Acrylate", J. Am. Chem. Soc., vol. 120, No. 5, pp. 888-899, (1998).
Ittel, S. D. et al., "Late-Metal Catalysts for Ethylene Homo- and Copolymerization", Chem. Rev., vol. 100, No. 4, pp. 1169-1203, (2000).
Braunstein, P. et al., "β-Keto Phosphines Derived From Ferrocene. Syntheses and Structures of [Ph$_2$ PCH$_2$ C(O)(ῆ$^5$ $^5$C $_5$H$_4$)Fe(ῆ$^5$ $^5$-C$_5$ H$_5$) ](L$^1$) and Trans-[PdCl$_2$ L$^1_2$]", JOM 09791, Journal of Organometallic Chemistry, vol. 367, pp. 117-132, (1989).

(Continued)

Primary Examiner — Rip A. Lee
(74) Attorney, Agent, or Firm — Oblon, Spivak, McClelland, Maier & Neustadt, L.L.P.

(57) ABSTRACT

A novel catalyst component for producing a crystalline α-olefin polymer or α-olefin/(meth)acrylate copolymer having few branches, especially a polymer having a high molecular weight, and a method for producing an α-olefin polymer or an α-olefin/(meth)acrylate copolymer using the catalyst component.

A metal complex represented by the following general formula (D), as well as a method for producing an α-olefin polymer and a method for producing an α-olefin/(meth)acrylate copolymer using the metal complex.

General Formula (D)

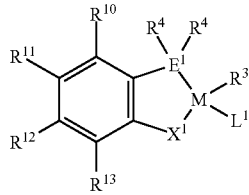

10 Claims, No Drawings

(56) References Cited

OTHER PUBLICATIONS

Bouaoud, S-E et al., "Complexes of Functional Phosphines. 10.[1] Palladium Complexes With the Ligands $Ph_2PCH_2COPh$, $(Ph_2PCHCOPh)$, and $Ph_2PCHC(Ph)OPPh_2$. Crystal and Molecular Structure of cis-$(PdCl_2\{Ph_2PCHC(Ph)OPPH_2\})]$", Inorg. Chem., vol. 25, No. 21, pp. 3765-3770, (1986).

Drent, E. et al., "Palladium Catalysed Copolymerisation of Ethene With Alkylacrylates: Polar Comonomer Built Into the Linear Polymer Chain", Chem. Commun., pp. 744-745, (2002).

Kochi, T. et al., "Synthesis of Anionic Methylpalladium Complexes With Phosphine-Sulfonate Ligands and Their Activities for Olefin Polymerization", Dalton Trans., pp. 25-27, (2006).

Klabunde, U. et al., "Ethylene Homopolymerization With P,O-Chelated Nickel Catalysts", Journal of Polymer Science: Part A: Polymer Chemistry, vol. 25, pp. 1989-2003, (1987).

Gibson, V. C. et al., "Functionalised Polyolefin Synthesis Using [P, O]Ni Catalysts", Chem. Commun., pp. 1964-1965, (Sep. 19, 2001).

International Search Report issued Jul. 7, 2009, in PCT/JP09/058263 filed Apr. 27, 2009.

European Search Report issued Feb. 27, 2012, in Patent Application No. 09823369.5.

Yasuhiro Yamamoto, et al., "Quasi-octahedral complexes of pentamethylcyclopenta-dienyliridium(III) bearing bis(diphenylphosphinomethyl)-phenylphosphine (dpmp)", J. Chem. Soc., Dalton Transactions, XP002669565, No. 18, 2004, pp. 2969-2978.

Ronan M. Bellabarba, et al., "Intramolecular Dehydrofluorinative Coupling of $\eta^5$-Pentamethylcyclopentadienyl and Pentafluorophenylphosphine Ligands in Rhodium Complexes", Organometallics, vol. 21, No. 26, XP002669566, 2002, pp. 5726-5737.

Combined Office Action and Search Report issued Apr. 28, 2013 in Chinese Patent Application No. 200980143250.8 with English language translation and English translation of categories of cited documents.

\* cited by examiner

METAL COMPLEX AND METHOD FOR PRODUCING α-OLEFIN POLYMER AND METHOD FOR PRODUCING α-OLEFIN/(METH)ACRYLATE COPOLYMER USING THE SAME

CROSS-REFERENCE TO RELATED APPLICATIONS

This application is a National Stage of PCT/JP2009/058263 filed on Apr. 27, 2009. This application is based upon and claims the benefit of priority to Japanese Application No. 2008-280388 filed on Oct. 30, 2008.

FIELD OF THE INVENTION

The present invention relates to a reaction product and a metal complex useful for producing an α-olefin polymer and an α-olefin/(meth)acrylate copolymer, and a novel method for producing an α-olefin polymer and a novel method for producing an α-olefin/(meth)acrylate copolymer using the same.

DESCRIPTION OF THE PRIOR ART

A method for copolymerizing ethylene and vinyl monomer containing a polar group, e.g. vinyl acetate and (meth)acrylate, by radical polymerization at high temperature under high pressure has been well known. This method, however, has a problem that the resultant copolymer has a low strength because a copolymer having low crystallinity is produced due to formation of many branches.

In addition, Brookhart et al have reported that ethylene/acrylate copolymer can be produced by using a palladium complex using α-diimine ligand as a catalyst. However, the resultant copolymer was rich in branched structure, and the branch was the one having various numbers of carbon atoms, e.g. methyl group and ethyl group, and number of the branch is very large. As a result, the resultant copolymer was the one having low crystallinity (for example, see Non-Patent Literature 1).

It has been also known that ethylene can be polymerized in a polar solvent, and a linear polymer having less branches can be obtained by using a nickel catalyst using a ligand having phosphorus and oxygen as coordination atoms, so called SHOP type catalyst. In the expectation for such resistance to polar group of the SHOP type catalyst, copolymerization of ethylene and polar monomer using the SHOP type catalyst has been tried. However, it has been reported that progression of the copolymerization with ethylene is limited to a case when a polar group in the polar monomer is located far from the olefin, and an example of copolymerization of (meth)acrylate in which a polar group binds directly to olefin and α-olefin has not been reported (for example, see Non-Patent Literature 2 and Patent Literature 1). It should be noted that, as an exceptional case, Gibson, et al. have performed copolymerization of ethylene and methyl methacrylate using a nickel catalyst of the SHOP type (for example, see Non-Patent Literature 8), but biscyclooctadiene nickel [Ni(COD)$_2$] as a phosphine scavenger was required for catalyst constitution component, and also methyl methacrylate was present only in the terminal of the polymer and was not incorporated in the main chain other than the terminal.

On the other hand, a method for copolymerizing ethylene and unsaturated carboxylate using a catalyst consisting of a combination of a similar SHOP type nickel (0 valence) chelate complex and aluminoxane has been disclosed (for example, see Patent Literature 2). In Example of this Patent Literature, an example of copolymerization of ethylene and methyl acrylate has been described, however, due to formation of an amorphous polymer as byproduct, it was necessary to remove said amorphous polymer by acetone extraction. In addition, concerning the resultant copolymer, there was only description on content of methyl acrylate, and no description on structure thereof.

It has been reported that a copolymer of ethylene and methyl acrylate can be obtained by using a palladium complex having phosphinosulfonic acid ligand as a catalyst, by Pugh et al. (for example, see Non-Patent Literature 5), Nozaki et al. (for example, see Non-Patent Literature 6), and Goodall et al. (for example, see Patent Literature 3). However, since the catalysts which were used in these known literatures use palladium which is a rare and precious resource, there is a big problem for an industrial application thereof.

As mentioned above, development of a transition metal catalyst technology useful for copolymerization of an olefin and an acrylate has been demanded, but generally, when olefin is polymerized using a single-site catalyst, molecular weight tends to be hardly increased, in comparison with the case using the conventional Ziegler-Natta catalyst. For this reason, development of a technology to increase molecular weight of an olefin polymer or an olefin/acrylate copolymer has been also demanded.

PRIOR ART LITERATURES

Patent Literatures

Patent Literature 1: U.S. Pat. No. 4,698,403
Patent Literature 2: JP-A-64-14217
Patent Literature 3: US Patent Application No. 2007/0049712

Non-Patent Literatures

Non-Patent Literature 1: S. Mecking et al., "J. Am. Chem. Soc.", 1998, 120, 888.
Non-Patent Literature 2: S. D. Ittel et al., "Chem. Rev.", 2000, 100, 1169.
Non-Patent Literature 3: P. Braunstein et al., "J. Organomet. Chem.", 1989, 367, 117.
Non-Patent Literature 4: S. E. Bauaoud et al., "Inorg. Chem.", 1986, 25, 3765.
Non-Patent Literature 5: E. Drent et al., "Chem. Commun.", 2002, 744.
Non-Patent Literature 6: T. Kochi et al., "Dalton Trans.", 2006, 25.
Non-Patent Literature 7: U. Klabunde et al., "J. Polym. Sci.: Part A: Polym. Chem.", 1987, 25, 1989.
Non-Patent Literature 8: V. C. Gibson, "Chem. Commun.", 2001, 1964.

SUMMARY OF INVENTION

Problem to be Solved by the Invention

Under such situation, problems to be solved by the present invention is to provide a novel catalyst component for production of a crystalline α-olefin polymer or α-olefin/(meth)acrylate copolymer having few branches, especially for production of a polymer having a high molecular weight, and a method for producing an α-olefin polymer or an α-olefin/(meth)acrylate copolymer using the same.

Means for Solving the Problem

The inventors of the present invention have found, after intensively studying, that when polymerization of α-olefin or copolymerization of α-olefin and (meth)acrylate is carried out using, as a catalyst component, a transition metal complex using a ligand having a specified structure, that is, a ligand having an aryl group as a scaffold, wherein at least one of two substituents $R^4$ on phosphorus, arsenic or antimony (described as $E^1$ in the present invention) bound to said aryl group is an aryl group containing two or more hetero atoms, a polymer having dramatically high molecular weight can be obtained, and accomplished the present invention.

That is, according to the first aspect of the present invention, a metal complex represented by the following general formula (D) is provided.

[Formula 1]

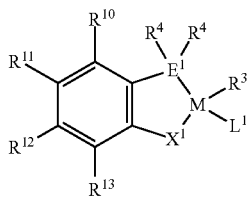

General Formula (D)

[In the general formula (D), M represents a transition metal belonging to $9^{th}$, $10^{th}$ or $11^{th}$ group in the periodic table. $R^3$ represents hydrogen or hydrocarbon group having 1 to 20 carbon atoms and optionally containing a hetero atom. $L^1$ represents a ligand coordinated to M. In addition, $R^3$ and $L^1$ may bind each other to form a ring. $X^1$ represents oxygen or sulfur. $E^1$ represents phosphorus, arsenic or antimony. $R^4$ represents each independently hydrogen or hydrocarbon group having 1 to 20 carbon atoms and optionally containing a hetero atom, wherein at least one of $R^4$ is hydrocarbon group having two or more hetero-atom-containing groups. $R^{10}$, $R^{11}$, $R^{12}$ and $R^{13}$ represent each independently hydrogen, halogen, hydrocarbon group having 1 to 30 carbon atoms and optionally containing a hetero atom, $OR^2$, $CO_2R^2$, $CO_2M'$, $C(O)N(R^1)_2$, $C(O)R^2$, $SR^2$, $SO_2R^2$, $SOR^2$, $OSO_2R^2$, $P(O)(OR^2)_{2-y}(R^1)_y$, CN, $NHR^2$, $N(R^2)_2$, $Si(OR^1)_{3-x}(R^1)_x$, $OSi(OR^1)_{3-x}(R^1)_x$, $NO_2$, $SO_3M'$, $PO_3M'_2$, $P(O)(OR^2)_2M'$ or epoxy containing group. Here, $R^1$ represents hydrogen or hydrocarbon group having 1 to 20 carbon atoms. In addition, $R^2$ represents hydrocarbon group having 1 to 20 carbon atoms. M' represents alkali metal, alkaline earth metal, ammonium, quaternary ammonium or phosphonium, x represents an integer of 0 to 3, and y represents an integer of 0 to 2. It should be noted that, a plurality of groups properly selected from $R^4$, $R^{10}$, $R^{11}$, $R^{12}$ and $R^{13}$ may bind each other to form aliphatic ring, aromatic ring, or hetero ring containing hetero atom selected from oxygen, nitrogen and sulfur. In this case, number of ring member is 5 to 8, and the ring optionally has substituent thereon.]

In addition, according to the second aspect of the present invention, in the first aspect, a metal complex in which M in the general formula (D) is nickel (II), palladium (II), platinum (II), cobalt (II) or rhodium (III), is provided.

Further, according to the third aspect of the present invention, in the first aspect, a metal complex in which M in the general formula (D) is a transition metal belonging to $10^{th}$ group in the periodic table, is provided.

Further, according to the fourth aspect of the present invention, a method for producing a metal complex obtainable by contacting a compound represented by the following general formula (A) or (B) and a transition metal complex (C) containing a transition metal belonging to $9^{th}$, $10^{th}$ or $11^{th}$ group in the periodic table, is provided.

[Formula 2]

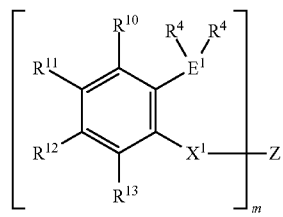

General Formula (A)

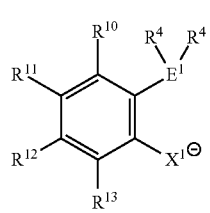

General Formula (B)

[In the general formula (A) and (B), Z represents hydrogen or elimination group. m represents valence of Z. $X^1$, $E^1$, $R^4$, $R^{10}$, $R^{11}$, $R^{12}$ and $R^{13}$ are same as aforementioned in the first aspect.]

In addition, according to the fifth aspect of the present invention, a method for producing α-olefin polymer, characterized in that (a) α-olefin is polymerized in the presence of the metal complex according to the first aspect, is provided.

In addition, according to the sixth aspect of the present invention, in the production method according to the fifth aspect, the method for producing α-olefin polymer, characterized in that polymerization is carried out in the presence of Lewis base, is provided.

Further, according to the seventh aspect of the present invention, in the production method according to the fifth aspect, the method for producing α-olefin polymer, characterized in that polymerization is carried out in the absence of organic aluminium compound, is provided.

Further, according to the eighth aspect of the present invention, a method for producing α-olefin/(meth)acrylate copolymer, characterized in that (a) α-olefin and (b) (meth)acrylate are copolymerized in the presence of the metal complex according to the first aspect, is provided.

Further, according to the ninth aspect of the present invention, in the production method according to the eighth aspect, the method for producing α-olefin/(meth)acrylate copolymer, characterized in that polymerization is carried out in the presence of Lewis base, is provided.

Further, according to the tenth aspect of the present invention, in the production method according to the eighth aspect, the method for producing α-olefin/(meth)acrylate copolymer, characterized in that polymerization is carried out in the absence of organic aluminium compound, is provided.

Effects of the Invention

According to the present invention, production of a copolymer of (meth)acrylate and α-olefin which are industrially easily available becomes possible and also molecular weight of the resultant polymer is high. Not only a copolymer, but also an α-olefin polymer can have a high molecular weight. Generally, molecular weight is one of dominant factors in physical properties of polymer, and interaction among polymer chains is strengthened by increasing molecular weight, therefore, the polymer or copolymer obtained by the present invention is superior in mechanical and thermal properties, and applicable as a useful molded product. Furthermore, in the present invention, a catalyst using nickel as a metal center instead of rare and precious palladium can be used. Thus, the present invention provides a novel method for producing such α-olefin polymer and α-olefin/(meth)acrylate copolymer, and is industrially extremely useful.

MODE FOR CARRYING OUT THE INVENTION

The present invention provides a reaction product and a metal complex (D) obtainable by reacting a specific compound (A) and/or (B) with a transition metal complex (C) containing a transition metal belonging to $9^{th}$, $10^{th}$ or $11^{th}$ group in the periodic table such as nickel, palladium, cobalt, copper or rhodium, and a method for producing a polymer of (a) α-olefin and a method for producing an α-olefin/(meth) acrylate copolymer by copolymerizing (a) α-olefin and (b) (meth)acrylate in the presence of the catalyst component, by using the metal complex (D) as a catalyst component. Hereinafter, constituent monomer of the polymer, catalyst component, production method, and the like will be described in detail.

It should be noted that, in the following description, the term "polymerization" means collectively homopolymerization of one kind of monomer and copolymerization of plural kinds of monomers, and both cases are described simply as "polymerization", especially when both cases need not be distinguished.

1. Constituent Monomer of the Polymer (a) α-Olefin

The component (a) in the present invention is α-olefin represented by the general formula $CH_2=CHR^7$. Here, $R^7$ is hydrogen or hydrocarbon group having 1 to 20 carbon atoms, which may have branch, ring and/or unsaturated bond. When carbon number of $R^7$ is larger than 20, polymerization activity tends to be less expressed. For this reason, among them, preferable component (a) includes α-olefins in which $R^7$ is hydrogen or hydrocarbon group having 1 to 10 carbon atoms.

Further preferable component (a) includes ethylene, propylene, 1-butene, 1-pentene, 1-hexene, 1-octene, 1-decene, 3-methyl-1-butene, 4-methyl-1-pentene, vinylcyclohexene and styrene. It should be noted that, single component (a) may be used or plural kinds of components (a) may be used in combination.

(b) (Meth)acrylate

The component (b) in the present invention is (meth)acrylate represented by the general formula $CH_2=C(R^8)CO_2(R^9)$. Here, $R^8$ is hydrogen or hydrocarbon group having 1 to 10 carbon atoms, which may have branch, ring and/or unsaturated bond. $R^9$ is hydrocarbon group having 1 to 30 carbon atoms, which may have branch, ring and/or unsaturated bond. Further, $R^9$ may contain a hetero atom at any position therein.

When carbon number of $R^8$ is larger than 11, polymerization activity tends to be less expressed. Therefore, $R^8$ is hydrogen or hydrocarbon group having 1 to 10 carbon atoms, and preferable component (b) includes (meth)acrylate in which $R^8$ is hydrogen or hydrocarbon group having 1 to 5 carbon atoms. More preferable component (b) includes methacrylate in which $R^8$ is methyl group or acrylate in which $R^8$ is hydrogen. Similarly, when carbon number of $R^9$ is larger than 30, polymerization activity tends to be less expressed. Therefore, carbon number of $R^9$ is 1 to 30, preferably 1 to 12, and further more preferably 1 to 8.

In addition, the hetero atom optionally contained in $R^9$ includes oxygen, sulfur, selenium, phosphorus, nitrogen, silicon, fluorine, boron, and the like. Among these hetero atoms, oxygen, silicon and fluorine are preferable, and oxygen is further more preferable. In addition, $R^9$ containing no hetero atom is also preferable.

Further more preferable component (b) includes methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, pentyl (meth)acrylate, hexyl (meth)acrylate, cyclohexyl (meth)acrylate, octyl (meth)acrylate, 2-ethylhexyl (meth)acrylate, nonyl (meth) acrylate, decyl (meth)acrylate, dodecyl (meth)acrylate, phenyl (meth)acrylate, toluoyl (meth)acrylate, benzyl (meth) acrylate, hydroxyethyl (meth)acrylate, dimethylaminoethyl (meth)acrylate, diethylaminoethyl (meth)acrylate, (meth) acrylate-2-aminoethyl, (meth)acrylate-2-methoxyethyl, (meth)acrylate-3-methoxypropyl, glycidyl (meth)acrylate, ethyleneoxide (meth)acrylate, trifluoromethyl (meth)acrylate, 2-trifluoromethylethyl (meth)acrylate, perfluoroethyl (meth)acrylate, (meth)acrylamide, (meth)acryldimethylamide, 2-hydroxybutyl (meth)acrylate, 4-hydroxybutyl (meth) acrylate, and the like. It should be noted that, the component (b) may be used alone or a plurality of components (b) may be used in combination.

2. Metal Complex

The reaction product of the present invention is represented by the following general formula (D):

[Formula 3]

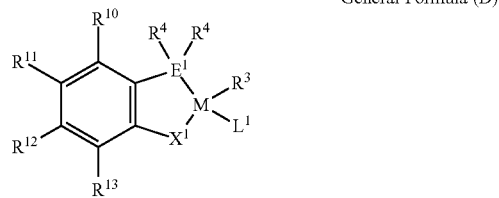

General Formula (D)

Here, M represents a transition metal belonging to $9^{th}$, $10^{th}$ or $11^{th}$ group in the periodic table. $R^3$ represents hydrogen or hydrocarbon group having 1 to 20 carbon atoms and optionally containing a hetero atom. $L^1$ represents a ligand coordinated to M. In addition, $R^3$ and $L^1$ may bind each other to form a ring. $X^1$ represents oxygen or sulfur. $E^1$ represents phosphorus, arsenic or antimony. $R^4$ represents each independently hydrogen or hydrocarbon group having 1 to 20 carbon atoms and optionally containing a hetero atom, wherein at least one of $R^4$ is hydrocarbon group having two or more hetero-atom-containing groups. $R^{10}$, $R^{11}$, $R^{12}$ and $R^{13}$ represent each independently hydrogen, halogen, hydrocarbon group having 1 to 30 carbon atoms and optionally containing a hetero atom, $OR^2$, $CO_2R^2$, $CO_2M'$, $C(O)N(R^1)_2$, $C(O)R^2$, $SR^2$, $SO_2R^2$, $SOR^2$, $OSO_2R^2$, $P(O)(OR^2)_{2-y}(R^1)_y$, $CN$, $NHR^2$, $N(R^2)_2$, $Si(OR^1)_{3-x}(R^1)_x$, $OSi(OR^1)_{3-x}(R^1)_x$, $NO_2$, $SO_3M'$, $PO_3M'_2$, $P(O)(OR^2)_2M'$ or epoxy containing group. Here, $R^1$ represents hydrogen or hydrocarbon group having 1 to 20 carbon atoms. In addition, $R^2$ represents hydrocarbon group having 1 to 20 carbon atoms. M' represents alkali metal, alkaline earth metal, ammonium, quaternary ammonium or phosphonium, x represents an integer of 0 to 3, and y represents an integer of 0 to 2. It should be noted that, a plurality of groups properly selected from $R^4$, $R^{10}$, $R^{11}$, $R^{12}$ and $R^{13}$ may bind each other to form aliphatic ring, aromatic ring, or hetero ring containing hetero atom selected from oxygen, nitrogen and sulfur. In this case, number of ring member is 5 to 8, and the ring optionally has substituent thereon.

In the present invention, M is a transition metal belonging to $9^{th}$, $10^{th}$ or $11^{th}$ group in the periodic table, and preferably nickel, palladium and platinum in $10^{th}$ group, cobalt and rhodium in $9^{th}$ group, and copper in $11^{th}$ group, and more preferably nickel, palladium and platinum in $10^{th}$ group, and most preferably nickel or palladium in $10^{th}$ group.

As for valence of M, divalent is preferable. Here, valence of M means formal oxidation number used in the organometallic chemistry. That is, when an electron pair in a bond in which certain elements are involved is assigned to an element having greater electronegativity, valence means a number of charge remained on an atom of the element. For example, in the general formula (D) of the present invention, when $E^1$ is phosphorus, $X^1$ is oxygen, M is nickel, $R^3$ is phenyl group, and $L^1$ is pyridine, wherein nickel forms bonds with phosphorus, oxygen, carbon of the phenyl group and nitrogen of pyridine, formal oxidation number of nickel, namely, valence of nickel becomes divalent. Because, according to the above-described definition, in these bonds, electron pairs are assigned to phosphorus, oxygen, carbon and nitrogen which have greater electronegativity than nickel, and charge of each group becomes 0 for phosphorus, −1 for oxygen, −1 for phenyl group, and 0 for pyridine, and the complex is electrically neutral as a whole, therefore, charge remaining on nickel becomes +2.

As a divalent transition metal, for example, nickel (II), palladium (II), platinum (II), and cobalt (II) are preferable, and as a transition metal other than divalent one, copper (I) or rhodium (III) is also preferable.

$R^3$ in the present invention represents hydrogen or hydrocarbon group having 1 to 20 carbon atoms and optionally containing a hetero atom. Polymerization or copolymerization in the present invention is considered to be initiated by inserting component (a) or component (b) in the present invention into the bond of M and $R^3$. Therefore, when number of carbon of $R^3$ is excessively large, this initiation reaction tends to be inhibited. For this reason, $R^3$ is hydrocarbon having preferably 1 to 16 carbon atoms, and more preferably 1 to 10 carbon atoms.

Specific example of $R^3$ includes hydride group, methyl group, ethyl group, n-propyl group, isopropyl group, n-butyl group, isobutyl group, n-hexyl group, n-octyl group, n-decyl group, n-dodecyl group, cyclopentyl group, cyclohexyl group, phenyl group, p-methylphenyl group, trimethylsilyl group, triethylsilyl group, triphenylsilyl group, and the like.

In the present invention, $L^1$ represents a ligand coordinated to M. The ligand $L^1$ in the present invention is a hydrocarbon compound having 1 to 20 carbon atoms having oxygen, nitrogen or sulfur as an atom capable of forming coordination bond. In addition, as $L^1$, a hydrocarbon compound having carbon-carbon unsaturated bond (and optionally containing a hetero atom) capable of forming coordination bond with a transition metal can be also used. Number of carbon of $L^1$ is preferably 1 to 16, and more preferably 1 to 10. In addition, as $L^1$ forming coordination bond with M in the general formula (D), a compound having no charge is preferable.

Although $L^1$ forms coordination bond with M, in the present invention, it is not necessary to use a compound (scavenger) which removes $L^1$ from M, in order to progress polymerization of component (a) or copolymerization of component (a) and component (b).

It should be noted that, in the case of so-called SHOP type metal complex, a complex similar to the one in the present invention can be synthesized even by using phosphine, for example, trimethylphosphine and triphenylphosphine, instead of $L^1$ in the present invention. However, it is known that when such ligand is used, it is essential for expressing polymerizing ability of olefin to use a scavenger to remove said ligand from M in combination (Non-Patent Literature 7). As the scavenger to be used for such purpose, $Ni(COD)_2$ (COD: cyclooctadiene), $B(C_6F_5)_3$, aluminoxanes, rhodium complex, and the like are known.

Preferable $L^1$ in the present invention includes pyridines, piperidines, alkylethers, arylethers, alkylarylethers, cyclic ethers, alkylnitrile derivative, arylnitril derivative, alcohols, amides, aliphatic esters, aromatic esters, amines, cyclic unsaturated hydrocarbons, and the like. More preferable $L^1$ can include pyridines, cyclic ethers, aliphatic esters, aromatic esters, and cyclic olefins, and particularly preferable $L^1$ can include pyridine, lutidine (dimethylpyridine), picoline (methylpyridine), $R^1CO_2R^2$ (definitions of $R^1$ and $R^2$ are as described above).

It should be noted that, $R^3$ and $L^1$ may bind each other to form a ring. Such an example can include cyclooct-1-enyl group, and this group is also preferable embodiment in the present invention.

In the present invention, $X^1$ represents oxygen or sulfur. Among these, oxygen is preferable. In addition, in the present invention, $E^1$ represents phosphorus, arsenic or antimony. Among these, phosphorus is preferable.

In the present invention, $R^4$ is each independently hydrocarbon group having 1 to 20 carbon atoms and optionally containing a hetero atom, wherein at least one of $R^4$ is hydrocarbon group containing two or more groups containing a hetero atom. $R^4$ is located in the neighborhood of the metal M, and affects M with steric and/or electronic interaction. To have such effect, $R^4$ is preferably bulky. $R^4$ has preferably 3 to 20 carbon atoms, and more preferably 6 to 20 carbon atoms.

In $R^4$, the hetero atom contained in the group containing a hetero atom includes oxygen, nitrogen, phosphorus, sulfur, selenium, silicon, fluorine, and boron. Among these hetero atoms, oxygen, silicon and fluorine are preferable. In addition, in the hetero-atom-containing group containing a hetero atom, oxygen-containing group includes alkoxy group, aryloxy group, acyl group, aroyl group and carboxylate group; nitrogen-containing group includes amino group and amide group; sulfur-containing group includes thioalkoxy group and thioaryloxy group; phosphorus-containing substitution group includes phosphino group; selenium-containing group includes selenyl group; silicon-containing group includes trialkylsilyl group, dialkylarylsilyl group and alkyldiarylsilyl group; fluorine-containing group includes fluoroalkyl group and fluoroaryl group; and boron-containing group includes alkylboron group and arylboron group. Among these hetero-atom-containing groups, most preferable group is alkoxy group or aryloxy group.

As the hetero atom contained in the aforementioned hetero-atom-containing group, the one capable of coordinating to a transition metal is preferable. Specific example of such hetero-atom-containing group containing a hetero atom capable of coordinating to a transition metal includes the following groups. That is, oxygen-containing group can include methoxy group, ethoxy group, n-propoxy group, iso-propoxy group, n-butoxy group, t-butoxy group, phenoxy group, p-methylphenoxy group, p-methoxyphenoxy group, acetyl group, benzoyl group, acetoxy group, ethylcarboxylate group, t-butylcarboxylate group, phenylcarboxylate group, and the like. Nitrogen-containing group can include dimethylamino group, diethylamino group, di-n-propylamino group, cyclohexylamino group, and the like. Sulfur-containing group can include thiomethoxy group, thioethoxy group, thio-n-propoxy group, thioisopropoxy group, thio-n-butoxy group, thio-t-butoxy group, thiophenoxy group, p-methylthiophenoxy group, p-methoxythiophenoxy group, and the like. Phosphorus-containing group can include dimethylphosphino group, diethylphosphino group, di-n-propylphosphino group, cyclohexylphosphino group, and the like. Selenium-containing group can include methylselenyl group, ethylselenyl group, n-propylselenyl group, n-butylselenyl group, t-butylselenyl group, phenylselenyl group, and the like.

In $R^4$, at least one $R^4$ may have two or more hetero-atom-containing groups, in particular, $R^4$ having two hetero-atom-containing groups is preferable. In addition, as for combination of $R^4$, there are two cases, that is, a case in which two $R^4$s have both two or more hetero-atom-containing groups and a case in which one $R^4$ has two or more hetero-atom-containing groups and the other one $R^4$ has one or no hetero-atom-containing group, and the case in which two $R^4$s have two or more hetero-atom-containing groups is preferable.

In the present invention, $R^4$ is each independently hydrogen or hydrocarbon group having 1 to 20 carbon atoms and optionally containing a hetero atom, more specifically, $R^4$ includes hydrogen or a linear hydrocarbon group optionally containing a hetero atom, a branched chain hydrocarbon group optionally containing a hetero atom, an alicyclic hydrocarbon group optionally containing a hetero atom, and an aryl group optionally containing a hetero atom. As described above, a bulky $R^4$ is preferable. Therefore, among these groups, an alicyclic hydrocarbon group optionally containing a hetero atom or an aryl group optionally containing a hetero atom is preferable, and an aryl group optionally containing a hetero atom is most preferable. Such aryl group includes phenyl group, naphthyl group, anthrathenyl group, and the like.

In $R^4$ of the present invention, when the aforementioned hetero-atom-containing group binds to an aromatic backbone of these aryl groups, as for binding mode, the hetero-atom-containing group may bind directly to the aromatic backbone, or may bind to the aromatic backbone via a spacer like methylene group. It should be noted that, when hetero-atom-containing group binds to an aromatic skeleton via methylene group, number of the methylene group is preferably one. In addition, as for position of substitution, ortho-position to the carbon binding to $E^1$ in the aromatic backbone of $R^4$ is preferable. By substituting in such manner, the hetero atom in $R^4$ can take a spatial configuration so as to have an interaction with M.

Specific example of preferable $R^4$ includes 2,6-dimethoxyphenyl group, 2,4,6-trimethoxyphenyl group, 4-methyl-2,6-dimethoxyphenyl group, 4-t-butyl-2,6-dimethoxyphenyl group, 1,3-dimethoxy-2-naphthyl group, 2,6-diethoxyphenyl group, 2,4,6-triethoxyphenyl group, 4-methyl-2,6-diethoxyphenyl group, 4-t-butyl-2,6-diethoxyphenyl group, 1,3-diethoxy-2-naphthyl group, 2,6-diphenoxyphenyl group, 2,4,6-triphenoxyphenyl group, 4-methyl-2,6-diphenoxyphenyl group, 4-t-butyl-2,6-diphenoxyphenyl group, 1,3-diphenoxy-2-naphthyl group, 2,6-dimethoxymethylphenyl group, 2,4,6-trim ethoxymethylphenyl group, 4-methyl-2,6-dimethoxymethylphenyl group, 4-t-butyl-2,6-dimethoxymethylphenyl group, 1,3-dimethoxymethyl-2-naphthyl group, 2,6-diphenoxymethylphenyl group, 2,4,6-triphenoxymethylphenyl group, 4-methyl-2,6-diphenoxymethylphenyl group, 4-t-butyl-2,6-diphenoxymethylphenyl group, 1,3-diphenoxymethyl-2-naphthyl group, 2,6-di(2-methoxyethyl) phenyl group, 2,4,6-tri(2-methoxyethyl)phenyl group, 4-methyl-2,6-di(2-methoxyethyl)phenyl group, 4-t-butyl-2,6-di (2-methoxyethyl)phenyl group, 1,3-di(2-methoxyethyl)-2-naphthyl group, 2,6-di(2-phenoxyethyl)phenyl group, 2,4,6-tri(2-phenoxyethyl)phenyl group, 4-methyl-2,6-di(2-phenoxyethyl)phenyl group, 4-t-butyl-2,6-di(2-phenoxyethyl)phenyl group, 1,3-di(2-phenoxyethyl)-2-naphthyl group, and the like.

$R^{10}$, $R^{11}$, $R^{12}$ and $R^{13}$ are same as aforementioned, as for $R^{11}$ among these groups, more bulky group is preferable because such group tends to give a polymer having higher molecular weight. Carbon number of $R^{11}$ is 1 to 30, and preferably 3 to 30. Specific example of $R^{11}$ includes hydrocarbon group such as methyl group, ethyl group, n-propyl group, isopropyl group, n-butyl group, isobutyl group, t-butyl group, phenyl group, 1-naphthyl group, 2-naphthyl group, 1-anthrathenyl group, 2-anthrathenyl group, 9-anthrathenyl group, 4-t-butylphenyl group, 2,4-di-t-butylphenyl group, 9-fluorenyl group and cyclohexyl group; and hetero-atom-containing hydrocarbon group such as trifluoromethyl group, trimethylsilyl group, triethylsilyl group, tri-n-propylsilyl group, triphenylsilyl group, 2,6-difluorophenyl group, 2,4,6-trifluorophenyl group, pentafluorophenyl group and cyclohexylamino group.

Among these groups, particularly preferable $R^{11}$ includes t-butyl group, trimethylsilyl group, phenyl group, 9-anthrathenyl group, 4-t-butylphenyl group, 2,4-di-t-butylphenyl group.

Hereinafter, the metal complex (D) of the present invention is exemplified below, but is not limited to the following examples. It should be noted that, in the following exemplification, Me represents methyl group, Et represents ethyl group, iPr represents isopropyl group, tBu represents tertiary-butyl group, and Cy represents cyclohexyl group.

[Formula 4]

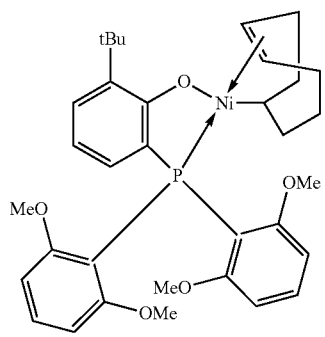

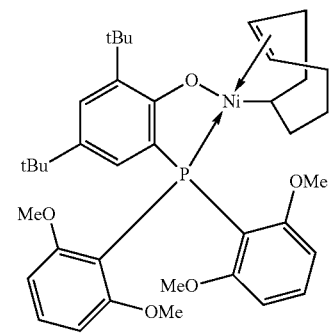

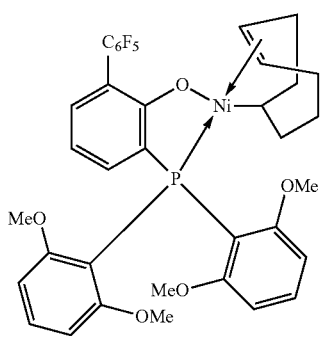
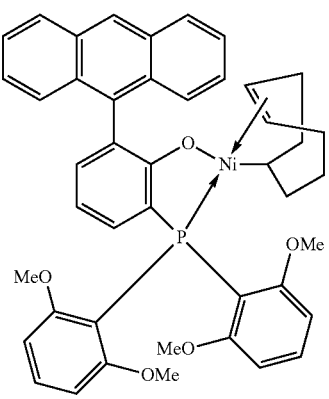
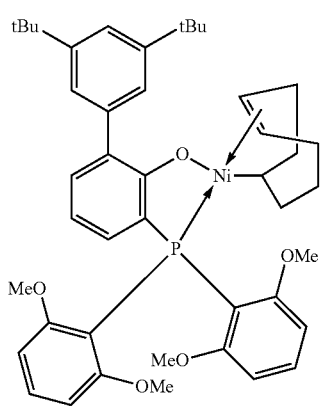
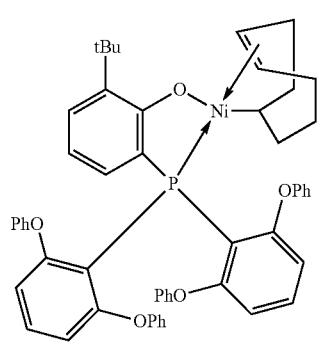
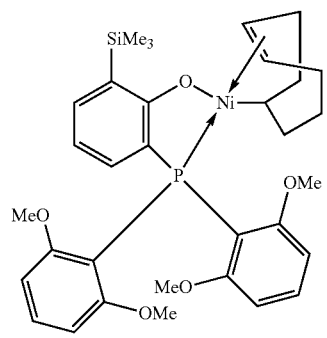
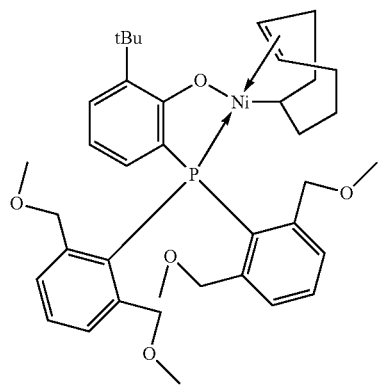
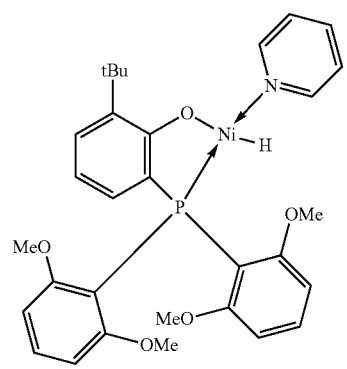
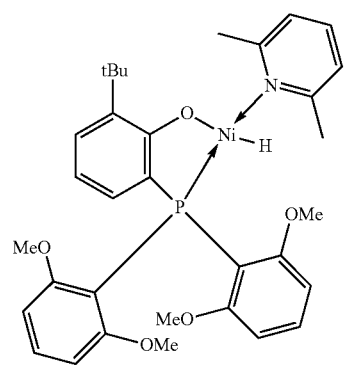

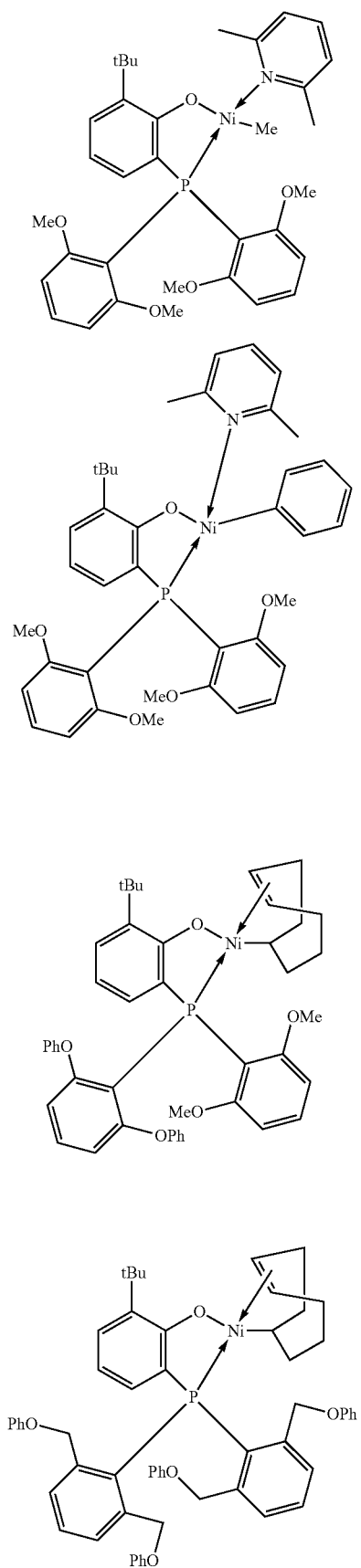
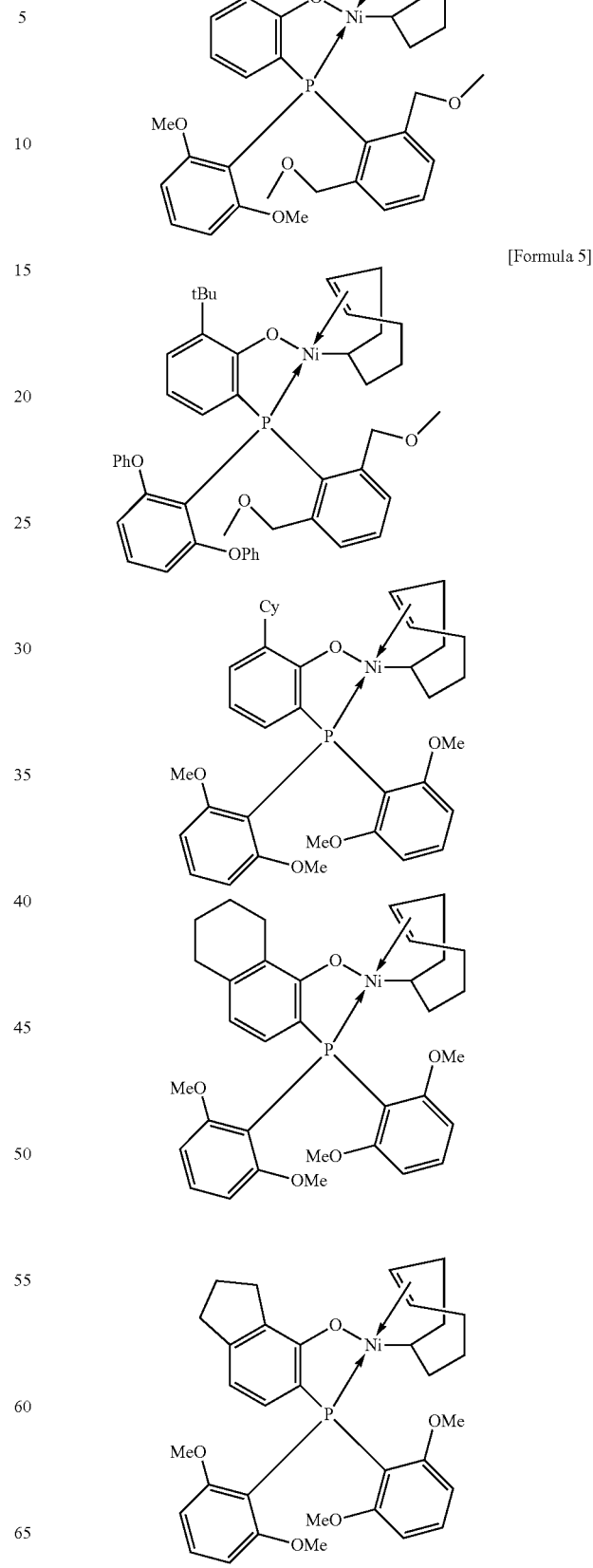
[Formula 5]

-continued
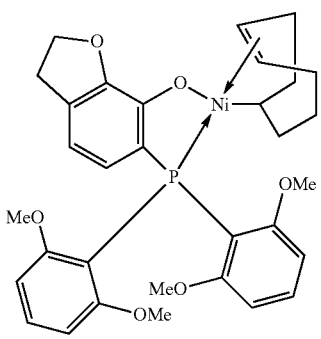
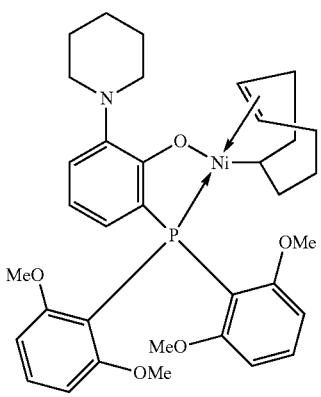
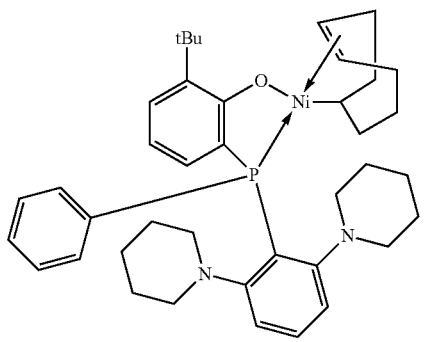
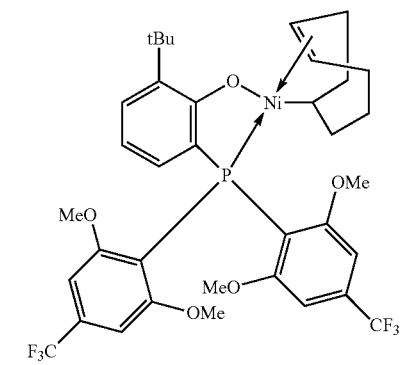
-continued
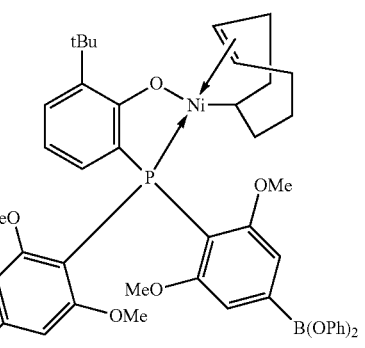
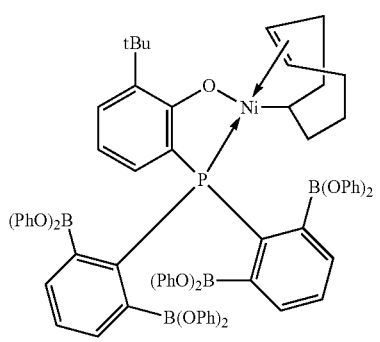
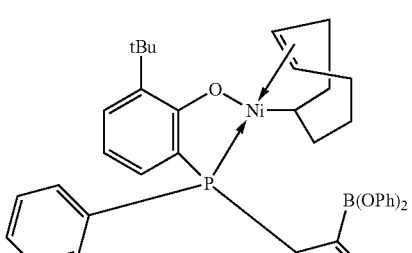
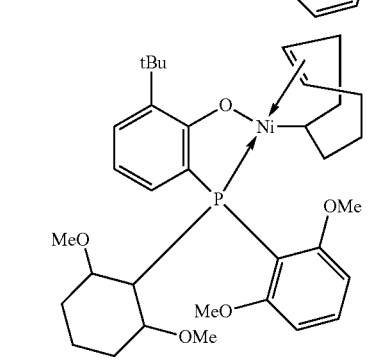
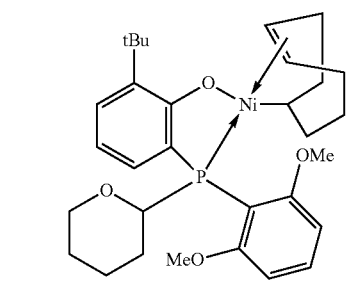

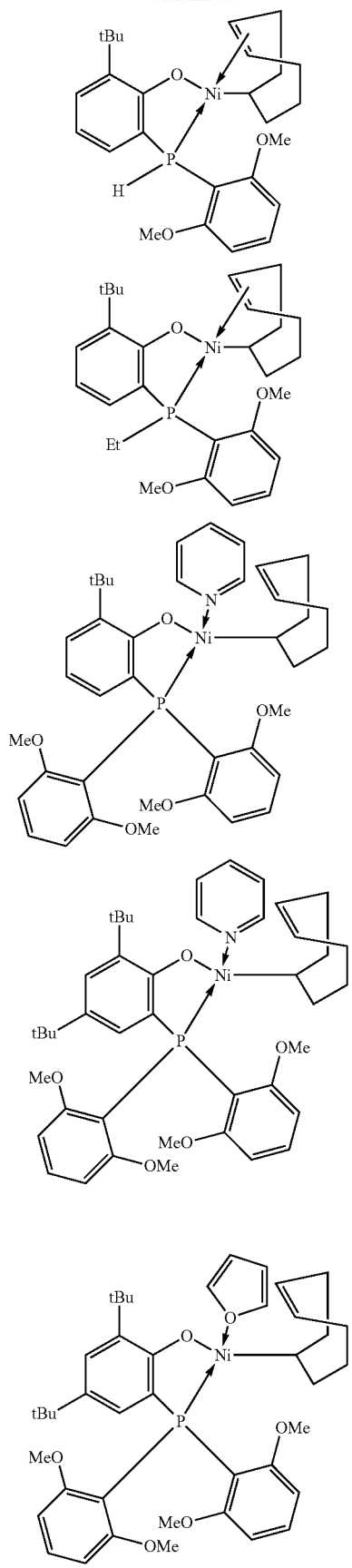

-continued
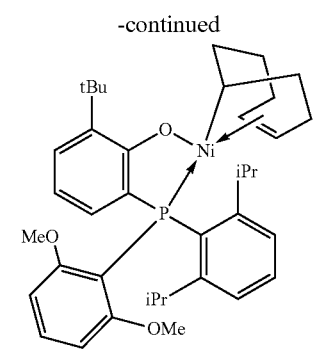
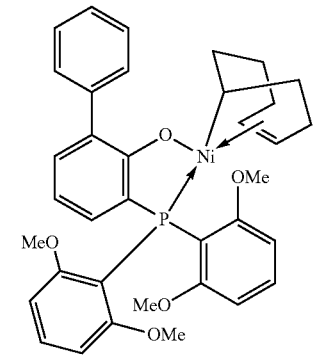
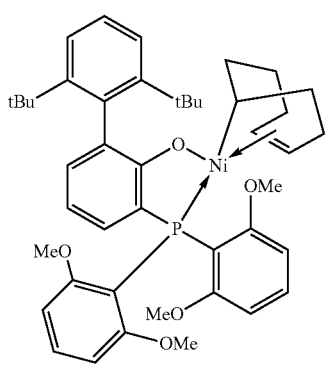
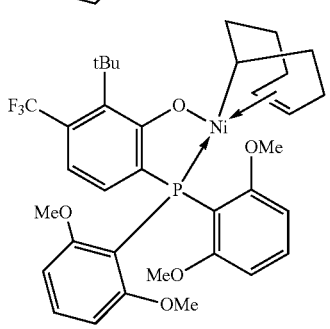
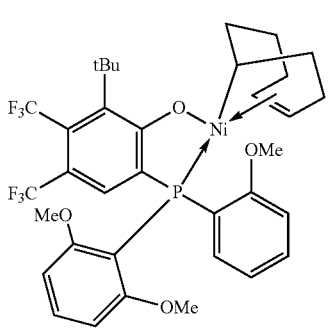
-continued
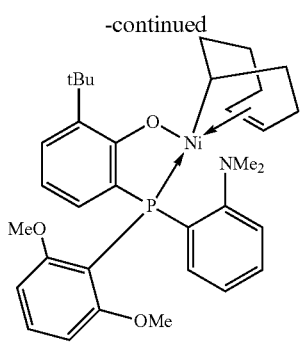
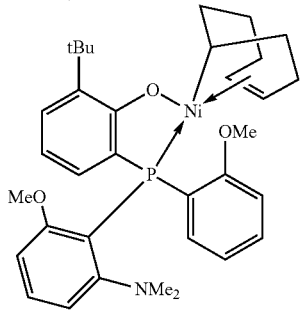
[Formula 7]
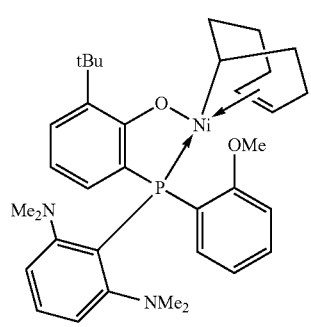
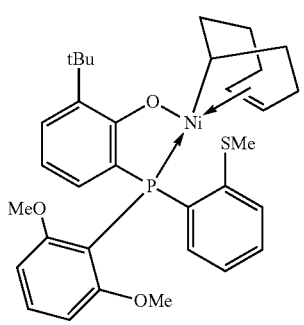
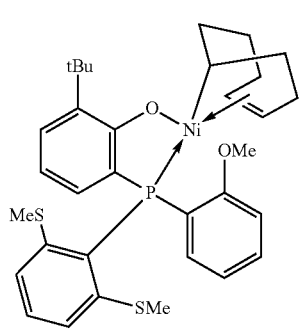

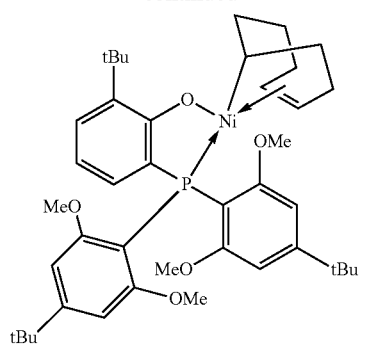

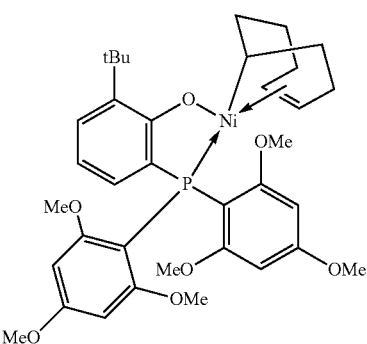

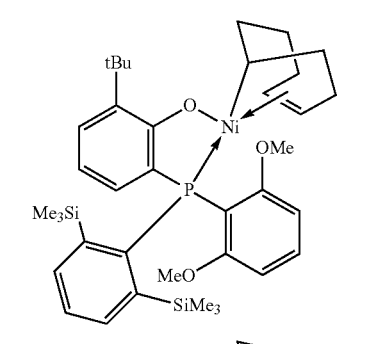

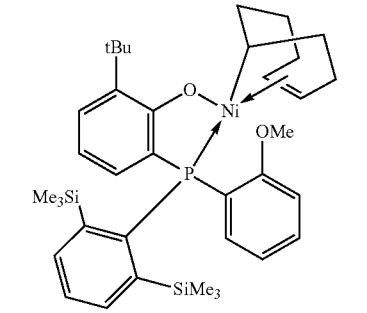

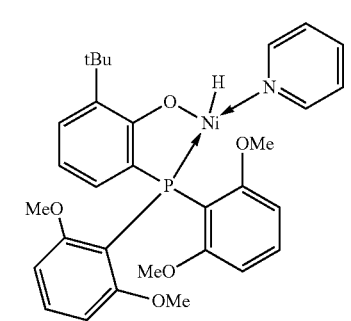

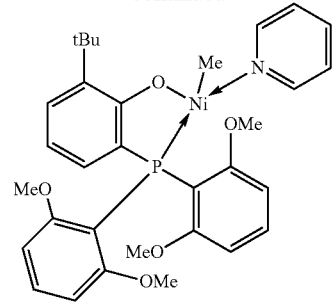

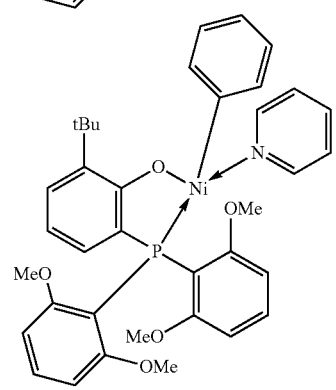

It should be noted that, depending on structure of ligand or complex forming conditions, stereo-isomer of the complex represented by the general formula (D) may be formed. Furthermore, M may take a coordination number other than 4. This is a kind of isomer. The complex of the present invention may be such isomers, and also a mixture of such isomers. Hereinafter, an example of the case when M takes a coordination number of 5 is shown.

[Formula 8]

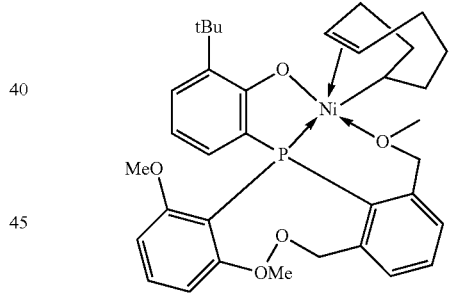

3. Production Method of Metal Complex

The complex of the present invention can be obtained by contacting a compound represented by the following general formula (A) and/or (B) with a transition metal complex (C) containing a transition metal belonging to $9^{th}$, $10^{th}$ or $11^{th}$ group.

[Formula 9]

General Formula (A)

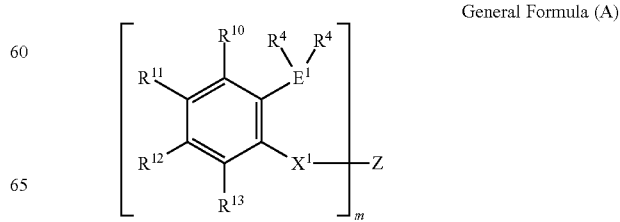

General Formula (B)

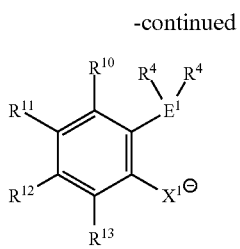

In the general formulas (A) and (B), Z is hydrogen or an elimination group. m represents valence of Z, and $X^1$, $E^1$, $R^4$, $R^{10}$, $R^{11}$, $R^{12}$ and $R^{13}$ are as aforementioned.

Z is hydrogen or an elimination group, and specifically can include hydrogen, $R^1SO_2$ group (wherein, $R^1$ is as aforementioned), $CF_3SO_2$ group, and the like.

Though the general formula (B) is shown in a form of anion, as the countercation thereof, any cation can be used, so long as the cation does not inhibit the reaction with the transition metal complex (C) of the present invention. Specifically, the counter cation can include ammonium, quaternary ammonium or phosphonium, and metal ion of $1^{st}$ to $14^{th}$ group of the periodic table. Among these cations, $NH_4^+$, $R^1{}_4N^+$ (wherein $R^1$ is as aforementioned, and four $R^1$s may be same or different from each other), $R^1{}_4P^+$ (wherein $R^1$ is as aforementioned and four $R^1$s may be same or different from each other), $Li^+$, $Na^+$, $K^+$, $Mg^+$, $Ca^{2+}$ and $Al^{3+}$ are preferable, and $R^1{}_4N^+$ (wherein $R^1$ is as aforementioned, and four $R^1$s may be same or different from each other), $Li^+$, $Na^+$ and $K^+$ are more preferable.

The substances represented by the general formulas (A) to (C) can be synthesized by a known synthesis method. The metal complex (D) is included in the reaction product between the compound represented by said (A) or (B) and the transition metal complex component (C) containing the metal M of the present invention.

As for the transition metal complex component (C) to be used in the present invention, those which are capable of forming a complex having polymerizing ability by reacting with a compound represented by the general formula (A) or (B) are used. These are sometimes referred to as precursor. For example, as the transition metal complex (C) containing nickel, bis-1,5-cyclooctadiene nickel (0), a complex represented by the general formula $(CH_2CR^1CH_2)_2Ni$ (wherein $R^1$ is as aforementioned), bis-cyclopentadienyl nickel (2), a complex represented by the general formula $Ni(CH_2SiR^1{}_3)_2L^1{}_2$ (wherein $R^1$ and $L^1$ are same as described herein), and a complex represented by the general formula $NiR^1{}_2L^1{}_2$ (wherein $R^1$ and $L^1$ are as described herein), and the like can be used.

In addition, as for the transition metal complex (C) containing a transition metal belonging to $9^{th}$, $10^{th}$ or $11^{th}$ group, the general formula $MR^{10}{}_pL^1{}_q$ (wherein M represents a transition metal of $9^{th}$, $10^{th}$ or $11^{th}$ group, $R^{10}$ and $L^1$ are as described herein, and p and q are each an integer 0 or more satisfying the valence of M) can be used.

Among these transition metal complexes, those to be used preferably include bis-1,5-cyclooctadiene nickel (0), a complex represented by the general formula $(CH_2CR^1CH_2)_2Ni$ (wherein $R^1$ is as described herein), a complex represented by the general formula $Ni(CH_2SiR^1{}_3)_2L^1{}_2$ (wherein $R^1$ and $L^1$ are as described herein), a complex represented by the general formula $NiR^1{}_2L^1{}_2$ (wherein $R^1$ and $L^1$ are described herein), $Pd(dba)_2$, $Pd_2(dba)_3$, $Pd_3(dba)_4$ (wherein dba represents dibenzylideneacetone), and $Pd(OCOCH_3)_2$.

Particularly preferable one includes bis-1,5-cyclooctadiene nickel (0), $(CH_2CHCH_2)_2Ni$, $(CH_2CMeCH_2)_2Ni$, $Ni(CH_2SiMe_3)_2(Py)_2$ (hereinafter, Py represents pyridine), $Ni(CH_2SiMe_3)_2(Lut)_2$ (hereinafter, Lut represents 2,6-lutidine), $NiPh_2(Py)_2$, $Ni(Ph)_2(Lut)_2$, $Pd(dba)_2$, $Pd_2(dba)_3$, $Pd_3(dba)_4$ (wherein dba represents dibenzylideneacetone), and $Pd(OCOCH_3)_2$.

The reaction product of the present invention can be obtained by contacting the aforementioned compound represented by the general formula (A) or (B) with the aforementioned transition metal complex (C), for example, in a molar ratio of (A)+(B): (C)=[1:99] to [99:1], in an organic solvent such as toluene at 0 to 100° C. for 1 to 86400 seconds under reduced pressure to increased pressure. When a solution of $Ni(COD)_2$ in toluene is used as (C), formation of the reaction product can be confirmed by change of color of the solution from yellow to, for example, red.

After the present reaction, a component, which is constructing (C) but is other than the transition metal of (C), is substituted by a part of the component (A) excluding Z or the component (B) to form the complex (D) of the present invention. This substitution reaction preferably proceeds quantitatively, but may sometimes proceed incompletely. After completion of the reaction, although other components derived from (A), (B) and (C) are present other than the complex (D), these other components may be removed or not removed when the polymerization reaction or copolymerization reaction of the present invention is carried out. Generally, these other components are preferably removed because higher activity can be obtained.

It should be noted that, when the reaction is carried out, $L^1$ of the present invention may exist together. When nickel or palladium is used as M of the present invention, stability of the formed complex (D) is sometimes improved by coexistence of $L^1$ having a nature of Lewis base in the system, in such case, coexistence of $L^1$ is preferable, so long as $L^1$ does not inhibit the polymerization reaction or copolymerization reaction of the present invention.

In the present invention, the reaction may be conducted in a vessel other than the reactor which is used for polymerization of α-olefin or copolymerization of α-olefin and (meth)acrylate, in advance, and then the resultant complex (D) may be used for polymerization of α-olefin or copolymerization of α-olefin and (meth)acrylate, or the reaction may be carried out in the presence of these monomers. In addition, the reaction may be conducted in the reactor which is used for polymerization of α-olefin or copolymerization of α-olefin and (meth)acrylate. In this case, these monomers may be present or absent. In addition, as for the components represented by the general formulas (A) to (C), each single component may be used, or each plural kinds of components may be used in combination. In particular, for the purposes to broaden molecular weight distribution or comonomer content distribution, such combined use of plural kinds of components is useful.

Hereinafter, (A) which can be used in the present invention is exemplified, but (A) is not limited to the following examples. It should be noted that, in the following exemplification, Et represents ethyl group, iPr represents isopropyl group, Ph represents phenyl group, Cy represents cyclohexyl group, and tBu represents tertiary-butyl group.

[Formula 10]

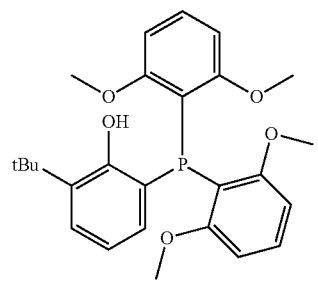

-continued
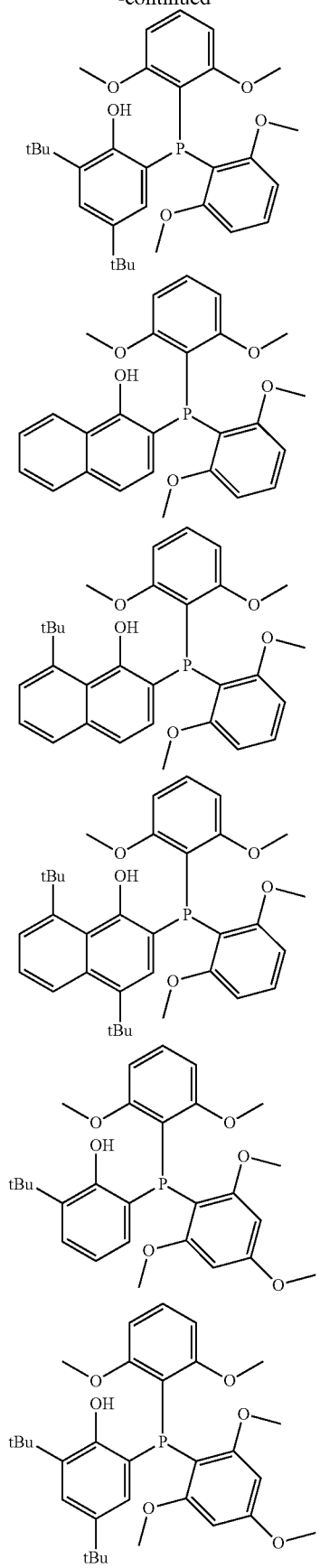
-continued
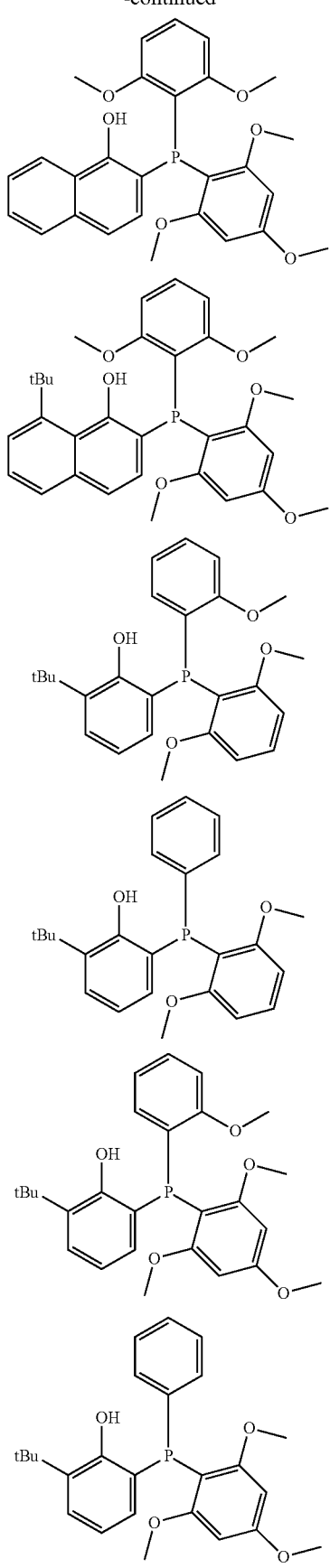

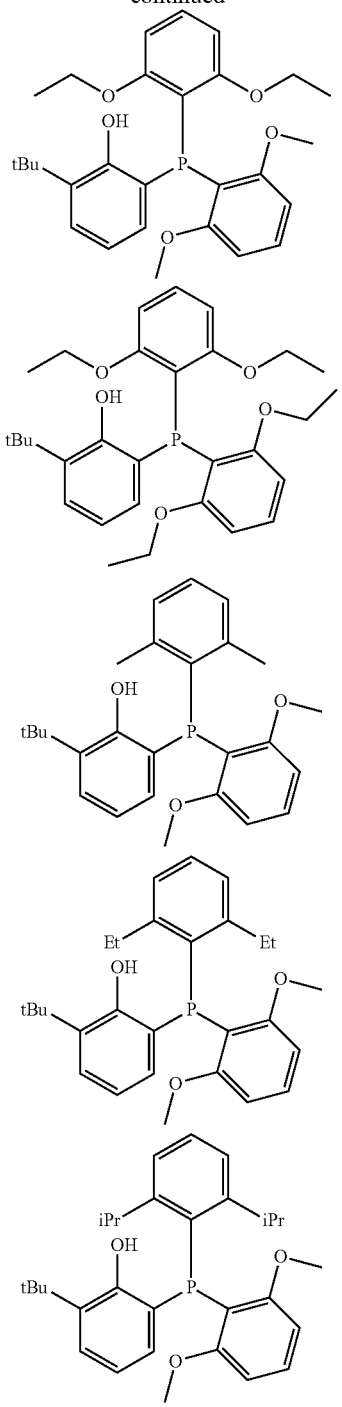
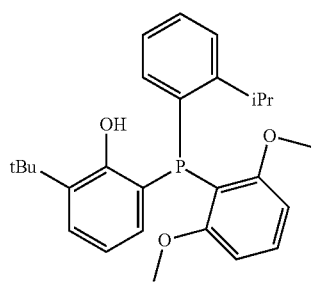
[Formula 11]
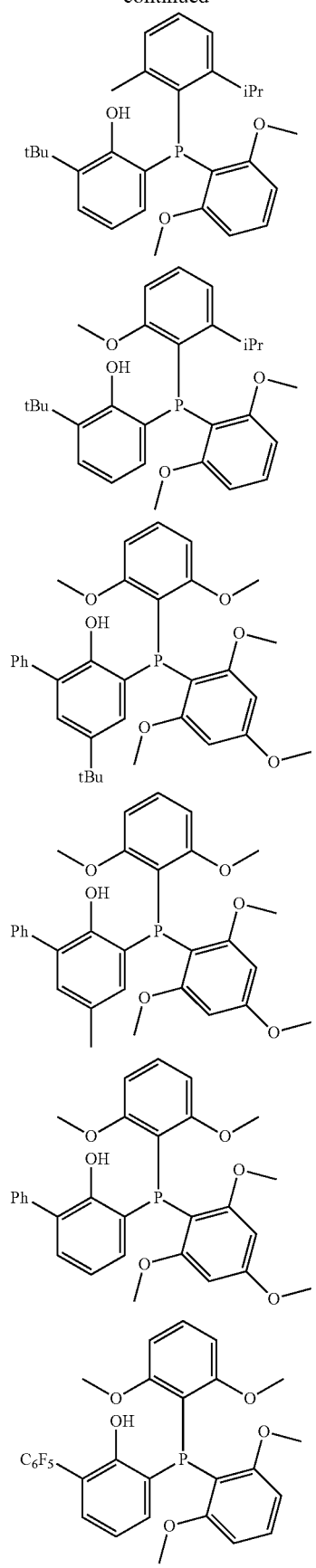

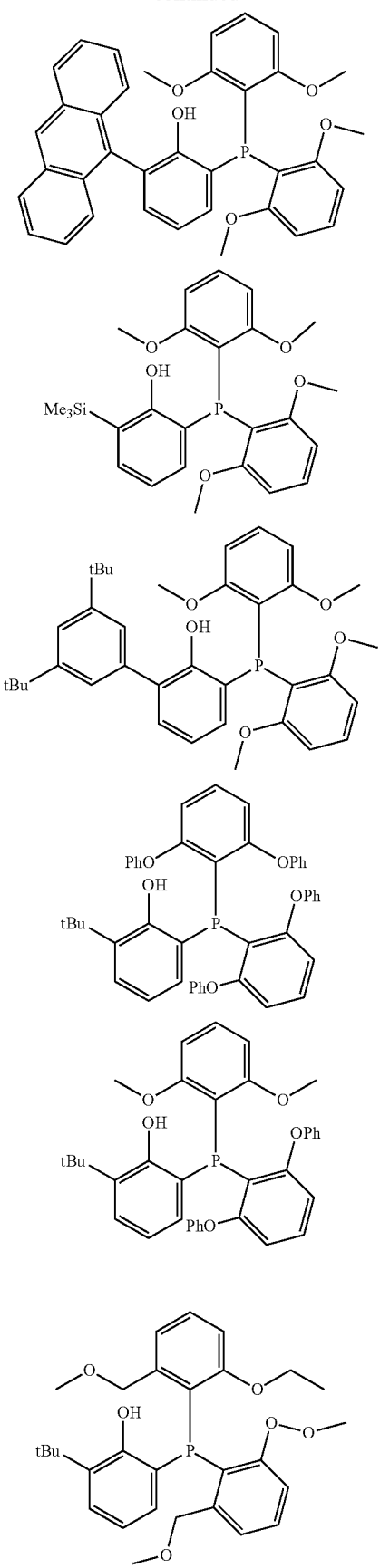
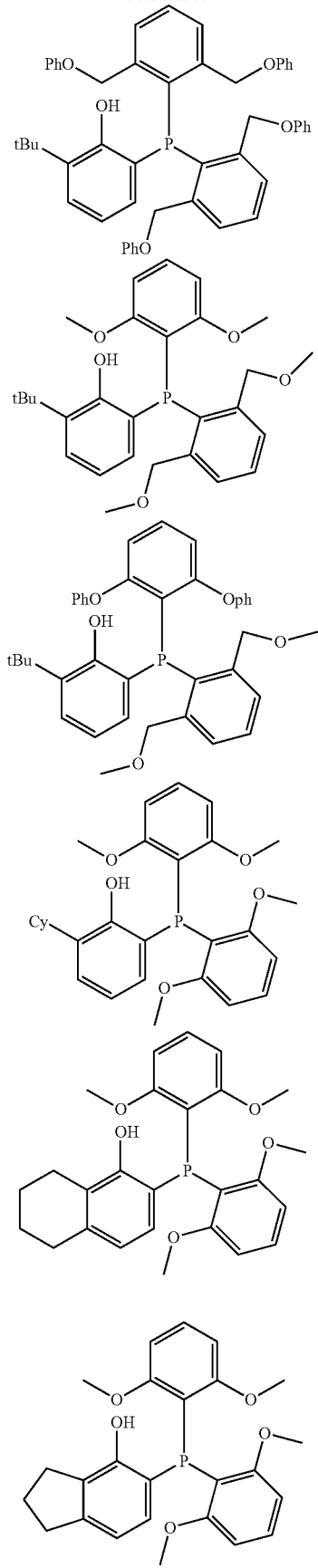
[Formula 12]

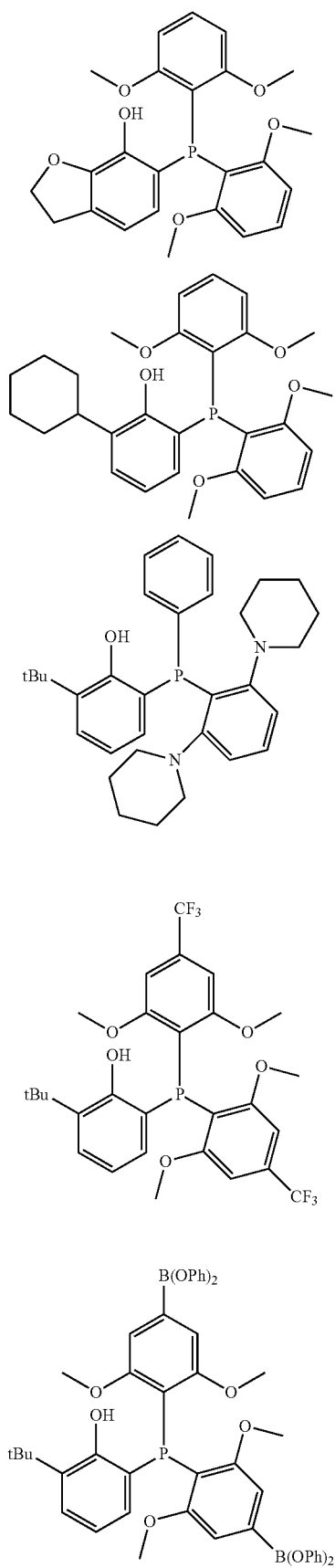
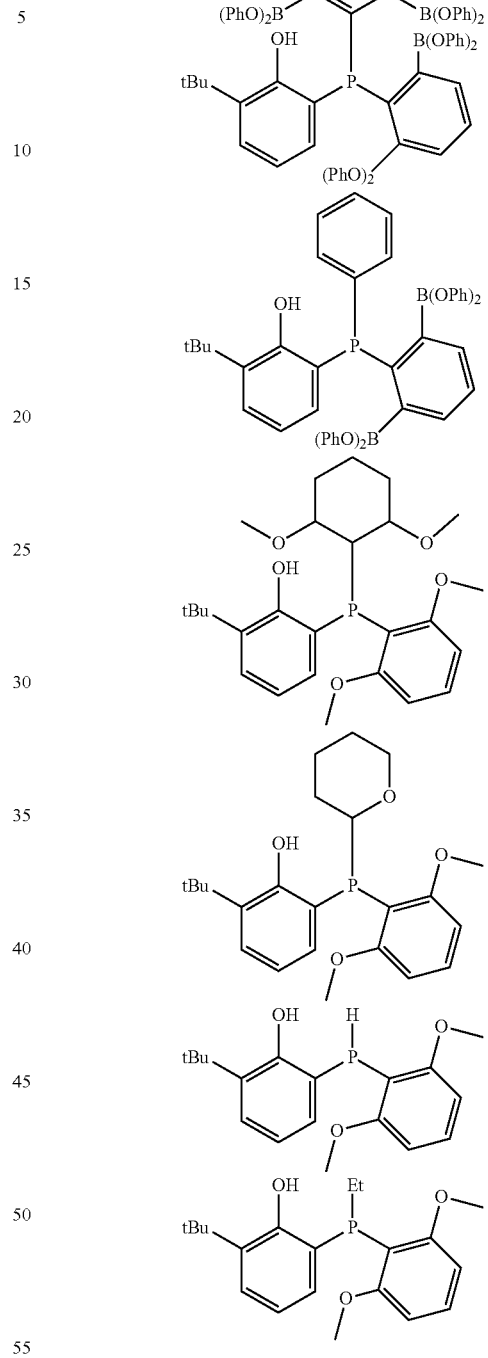

4. Polymerization Reaction

In the present invention, the metal complex represented by the general formula (D) can be used as a catalyst component for the polymerization or copolymerization. As aforementioned, the metal complex represented by the general formula (D) can be formed by reacting the general formula (A) or (B) with the transition metal complex component (C). When the compound represented by the general formula (D) is used as a catalyst component, the isolated one may be used or the one supported on a carrier may be used. Such supporting may be carried out in a reactor which is used for polymerization of α-olefin or copolymerization of α-olefin and (meth)acrylate, in the presence or the absence of these monomers, or may be carried out in a vessel other than said reactor.

As a usable carrier, any carrier can be used so long as the carrier does not impair the gist of the present invention. Generally, inorganic oxides and polymer carriers can be suitably used. Specifically the carrier includes $SiO_2$, $Al_2O_3$, MgO, $ZrO_2$, $TiO_2$, $B_2O_3$, CaO, ZnO, BaO, $ThO_2$, and the like, or a mixture thereof, also, mixed oxide such as $SiO_2$—$Al_2O_3$, $SiO_2$—$V_2O_5$, $SiO_2$—$TiO_2$, $SiO_2$—MgO and $SiO_2$—$Cr_2O_3$ can be used, and inorganic silicates, polyethylene carrier, polypropylene carrier, polystyrene carrier, polyacrylic acid carrier, polymethacrylic acid carrier, polyacrylate carrier, polyester carrier, polyamide carrier, polyimide carrier, and the like can be used. As for these carriers, particle diameter, particle diameter distribution, pore volume, specific surface area and the like are not particularly limited, and any carrier can be used.

As the inorganic silicate, clay, clay mineral, zeolite, diatomaceous earth, and the like can be used. For these substances, synthetic material may be used or naturally occurring mineral may be used. Specific example of clay and clay mineral includes allophane group such as allophane; kaoline group such as dickite, nacrite, kaolinite and anorthite; halloysite group such as metahalloysite and halloysite; serpentine group such as chrysotile, lizardite and antigorite; smectite such as montmorillonite, sauconite, beidellite, nontronite, saponite and hectorite; vermiculite minerals such as vermiculite; mica minerals such as illite, sericite and glauconite; attapulgite; sepiolite; palygorskite; bentnite; Kibushi clay; Gaerome clay; hisingerite; pyrophyllite; chlorite group; and the like. These substances may form a mixed layer. Artificial compounds include synthetic mica, synthetic hectorite, synthetic saponite, synthetic taeniolite, and the like. Among these specific examples, preferable one includes kaoline group such as dickite, nacrite, kaolinite and anorchisite; halloysite group such as metahalloysite and halloysite; serpentine group such as chrysotile, lizardite and antigorite; smectite such as montmorillonite, zaukonite, beidellite, nontronite, saponite and hectorite; vermiculite minerals such as vermiculite; mica minerals such as illite, sericite and glauconite; synthetic mica; synthetic hectorite; synthetic saponite; and synthetic taeniolite. Particularly preferable one includes smectite such as montmorillonite, zaukonite, beidellite, nontronite, saponite and hectorite; vermiculite minerals such as vermiculite; synthetic mica; synthetic hectorite; synthetic saponite; and synthetic taeniolite.

These carriers may be used as they are, or may be subjected to acid treatment with hydrochloric acid, nitric acid, sulfuric acid, and the like, and/or salts treatment with LiCl, NaCl, KCl, $CaCl_2$, $MgCl_2$, $Li_2SO_4$, $MgSO_4$, $ZnSO_4$, $Ti(SO_4)_2$, $Zr(SO_4)_2$, $Al_2(SO_4)_3$, and the like. Said treatment may be carried out by mixing corresponding acid and base to form a salt in the reaction system. In addition, shape control such as pulverization and granulation or drying treatment may be conducted.

The polymerization reaction in the present invention is carried out in the presence or the absence of a liquid of hydrocarbon solvent such as propane, n-butane, isobutane, n-hexane, n-heptane, toluene, xylene, cyclohexane and methylcyclohexane, or liquefied α-olefin, and the like, as well as a polar solvent such as diethyl ether, ethylene glycol dimethyl ether, tetrahydrofuran, dioxane, ethyl acetate, methyl benzoate, acetone, methyl ethyl ketone, formamide, acetonitrile, methanol, isopropyl alcohol and ethylene glycol. In addition, a mixture of liquid compounds described here may be used as a solvent. Furthermore, ionic liquid can also be used as a solvent. The above-described hydrocarbon solvent and ionic liquid are more preferable to obtain higher polymerization activity and high molecular weight.

In the present invention, the polymerization reaction can be carried out in the presence or the absence of known additive. As the additive, a polymerization inhibitor to inhibit radical polymerization of the component (b) and an additive having an action to stabilize produced copolymer are preferable. For example, an example of preferable additive includes quinone derivative, hindered phenol derivative, and the like. Specifically, hydroquinone monomethyl ether, 2,6-di-t-butyl-4-methylphenol (BHT), reaction product of trimethylaluminium and BHT, reaction product of titanium (IV) alkoxide and BHT, and the like can be used. In addition, the polymerization may be carried out in the presence of inorganic and/or organic filler by using such filler as an additive. Furthermore, $L^1$ of the present invention or ionic liquid may be used as an additive.

Preferable additive in the present invention includes Lewis base. By selecting appropriate Lewis base, activity, molecular weight and copolymerization reactivity of acrylate can be improved. Amount of Lewis base is 0.0001 to 1000 equivalents, preferably 0.1 to 100 equivalents, and more preferably 0.3 to 30 equivalents relative to the transition metal M in the catalyst component present in the polymerization system. Method for adding Lewis base to the polymerization system is not particularly limited, and any technique can be used. For example, Lewis base may be added by mixing with the catalyst component of the present invention, or may be added by mixing with monomer, or may be added to the polymerization system independently from catalyst component and monomer. In addition, a plurality of Lewis bases may be used in combination. In addition, same Lewis base as $L^1$ of the present invention may be used or may be different.

Lewis base includes aromatic amines, aliphatic amines, alkyl ethers, aryl ethers, alkyl aryl ethers, cyclic ethers, alkyl nitriles, aryl nitriles, alcohols, amides, aliphatic esters, aromatic esters, phosphates, phosphites, thiophenes, thianthrenes, thiazoles, oxazoles, morpholines, cyclic unsaturated hydrocarbons, and the like. Among these, particularly preferable Lewis base includes aromatic amines, aliphatic amines, cyclic ethers, aliphatic esters and aromatic esters, among them, preferable Lewis bases are pyridine derivative, pyrimidine derivative, piperidine derivative, imidazole derivative, aniline derivative, piperidine derivative, triazine derivative, pyrrole derivative and furan derivative.

Specific Lewis base compound includes pyridine, pentafluoropyridine, 2,6-lutidine, 2,4-lutidine, 3,5-lutidine, pyrimidine, N,N-dimethylaminopyridine, N-methylimidazole, 2,2'-bipyridine, aniline, piperidine, 1,3,5-triazine, 2,4,6-tris (trifluoromethyl)-1,3,5-triazine, 2,4,6-tris(2-pyridyl)-s-triazine, quinoline, 8-methylquinoline, phenazine, 1,10-phenanthroline, N-methylpyrrole, 1,8-diazabicyclo-[5.4.0]-undeca-7-ene, 1,4-diazabicyclo-[2.2.2]-octane, triethylamine, benzonitrile, picoline, triphenylamine, N-methyl-2-pyrrolidone, 4-methylmorpholine, benzoxazole, benzothiazole, furan, 2,5-dimethylfuran, dibenzofuran, xanthene, 1,4-dioxane, 1,3,5-trioxane, dibenzothiophene, thianthrene, triphenylphosphonium cyclopentadienide, triphenylphosphite, triphenylphosphate, tripyrrolizinophosphine, tris(pyrrolizino)borane, and the like.

In the present invention, polymerization style is not particularly limited. Slurry polymerization in which at least a part of the produced polymer takes a form of slurry in a medium; bulk polymerization in which liquefied monomer itself is used as a medium; gas phase polymerization in which polymerization is carried out in a vaporized monomer; or high pressure ion polymerization in which at least a part of the produced polymer dissolves in a monomer liquefied at high temperature and high pressure; and the like are preferably used. In addition, any type of batch polymerization, semi-batch polymerization and continuous polymerization may be used. In addition, living polymerization or a polymerization occurring in conjunction with chain transfer may be carried out. Still further, chain shuttling or coordinative chain transfer polymerization (CCTP) may be carried out by using so-called chain transfer agent (CSA) in combination.

Unreacted monomer and medium may be used by separating from the produced polymer and recycling. In recycling, these monomer and medium may be reused with or without purification. For separation of the produced polymer from unreacted monomer and medium, hitherto known method can be used. For example, a method such as filtration, centrifugation, solvent extraction or reprecipitation with poor solvent can be used.

Polymerization temperature, polymerization pressure and polymerization time are not particularly limited, however, generally, optimum setting can be done from the following ranges considering productivity and process capacity. That is, polymerization temperature can be selected from a range of generally −20° C. to 290° C., and preferably 0° C. to 250° C., copolymerization pressure can be selected form a range of 0.1 MPa to 100 MPa, and preferably 0.3 MPa to 90 MPa, and polymerization time can be selected from a range of 0.1 minute to 10 hours, preferably 0.5 minute to 7 hours, and more preferably 1 minute to 6 hours.

In the present invention, polymerization is generally conducted under the atmosphere of an inert gas. For example, atmosphere of nitrogen, argon or carbon dioxide can be used, and nitrogen atmosphere is preferably used. It should be noted that, comingling of a small amount of oxygen or air is accepted.

Supply of catalyst and monomer to polymerization reactor is also not particularly limited, and various supplying methods can be employed corresponding to each purpose. For example, in the case of batch polymerization, such a technique can be employed that a predetermined amount of monomer is supplied into a polymerization reactor in advance, followed by supplying the catalyst. In this case, additional monomer or additional catalyst may be supplied to the polymerization reactor. In addition, in the case of continuous polymerization, such a technique can be employed that predetermined amounts of monomer and catalyst are supplied to polymerization reactor continuously or intermittently to carry out polymerization reaction continuously.

As for control of copolymer composition, generally such a method can be used that a plurality of monomers are supplied to the reactor, and copolymer composition is controlled by varying a ratio thereof. In addition, a method in which copolymer composition is controlled by utilizing a difference in monomer reactivity ratios depending on difference in catalyst structures, and a method in which copolymer composition is controlled utilizing polymerization temperature dependency of monomer reactivity ratio, are included.

For controlling molecular weight of polymer, hitherto known method can be used. That is, a method in which molecular weight is controlled by controlling polymerization temperature, a method in which molecular weight is controlled by controlling monomer concentrations, a method in which molecular weight is controlled by using a chain transfer agent, a method in which molecular weight is controlled by controlling ligand structure in the transition metal complex, and the like are included. When chain transfer agent is used, hitherto known chain transfer agent can be used. For example, hydrogen, metalalkyl, and the like can be used.

In addition, when component (b) itself works as a kind of chain transfer agent, molecular weight can be also adjusted by controlling a ratio of component (b) to component (a) or concentration of component (b). When molecular weight is adjusted by controlling ligand structure in transition metal complex, such a tendency can be utilized that molecular weight is generally improved by controlling kind, number and configuration of the hetero-atom-containing group in the aforementioned $R^4$, by arranging a bulky group around the metal M, or introducing a hetero atom into the aforementioned $R^{10}$ to $R^{13}$. It should be noted that, the electron-donating group is preferably arranged so that an electron-donating group such as aryl group and hetero-atom-containing substituent can have an interaction to the metal M. It can be generally judged whether such electron-donating group can have an interaction with the metal M or not, by measuring a distance between the electron-donating group and the metal M using a molecule model or molecular orbital calculation.

The copolymer of the present invention expresses superior painting characteristic, printability, antistatic performance, inorganic filler dispersibility, adhesive property to other resins, compatibility with other resins, and the like. Utilizing such properties, the copolymer of the present invention can be used for various applications. For example, the copolymer can be used for film, sheet, adhesive resin, binder, compatibilizing agent, wax, and the like.

EXAMPLES

The present invention is explained in detail in the following Examples and Comparative Examples, however the present invention is not limited thereto.

In the following Synthesis Examples, unless otherwise noted, operations were conducted under the purified nitrogen atmosphere, and dewatered and deoxygenated solvents were used.

1. Evaluation Method
(1) Tm and Tc: Determined by the Following DSC Measurement.

Using PYRIS Diamond DSC differential scanning calorimeter manufactured by PerkinElmer Inc., a sample (about 5 mg) was melted at 210° C. for 5 minutes, then the temperature was reduced to −20° C. at a rate of 10° C./min, and after the temperature was kept at −20° C. for 5 min., the temperature was raised to 210° C. at a rate of 10° C./min. to obtain a melting curve. The top temperature of the main exothermic peak in the temperature reducing step was defined as the crystallization temperature Tc. In addition, the peak top temperature of the main endothermic peak in the last temperature increasing step, which was carried out to obtain the melting curve, was defined as the melting point Tm.

(2) Weight Average Molecular Weight $M_w$, Number Average Molecular Weight $M_n$ and Molecular Weight Distribution $M_w/M_n$: Determined by the Following GPC Measurement.

Firstly, a sample (about 20 mg) was collected in a vial for the pretreatment unit PL-SP 260VS for the high temperature GPC manufactured by Polymer Laboratories Ltd, and o-Dichlorobenzene containing BHT as a stabilizer (concentration of BHT=0.5 g/L) was added thereto, and polymer concentration was adjusted to 0.1% by weight. The polymer was dissolved by heating at 135° C. in the above-described pretreatment unit PL-SP 260VS for the high temperature GPC, and filtered with a glass filter to prepare a sample solution. It should be noted that, no polymer was seized by the glass filter in GPC measurement of the present invention. Next, GPC measurement was carried out using GPCV 2000 manufactured by Waters equipped with TSKgel GMH-HT (30 cm×4 pieces) manufactured by Tosoh Corp. as a column and RI detector. The following measuring conditions were employed: injection amount of sample solution: about 520 (μl); column temperature: 135° C.; solvent: o-dichlorobenzene; and flow rate: 1.0 (ml/min). Calculation of molecular weight was carried out as follows. That is, commercially available monodisperse polystyrene was used as a standard sample, and a calibration curve on retention time versus molecular weight was prepared from viscosity formulas of said polystyrene standard sample and an ethylene polymer, and calculation of molecular weight was carried out based on said calibration curve. It should be noted that, as a viscosity formula, $[\eta]=K \times M^{\alpha}$ was used, and K=1.38E-4, α=0.70 for polystyrene, and K=4.77E-4, α=0.70 for ethylene polymer were used.

2. Ligand, Complex

Synthesis Example 1

Synthesis of Ligand B-14

Ligand B-14 was synthesized according to the following scheme.

[Formula 13]

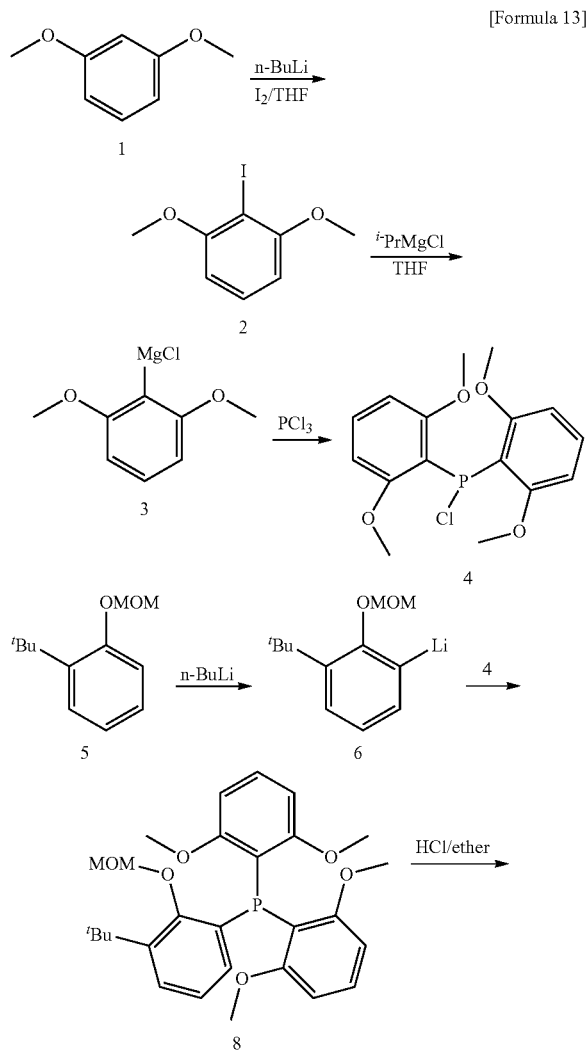

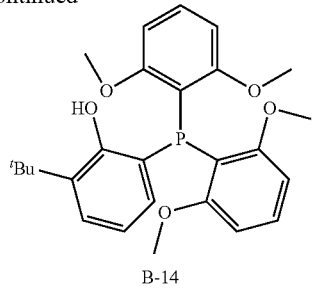

B-14

(1) Synthesis of Intermediate 2

2,6-Dimethoxybenzene 1 (50 g, 0.36 mol) was dissolved in absolute THF (500 ml). A solution of n-butyl lithium in n-hexane (166 ml, 0.42 mol) was slowly added thereto at 0° C. under the nitrogen atmosphere. To the resultant solution, a solution of iodine (96.5 g, 0.38 mol) dissolved in absolute THF (200 ml) was added dropwise at 0° C. over 40 minutes. The resultant solution was stirred at room temperature overnight. After completion of stirring, methanol (80 ml) was added dropwise, and the resultant mixture was concentrated under the reduced pressure, and after adding water (200 ml), the mixture was extracted with ethyl acetate (250 ml) 3 times. Organic layers were combined, and said organic layer was washed with $Na_2S_2O_3$ and brine, and then dried using sodium sulfate. After drying, inorganic salt was filtered off, and the filtrate was concentrated under the reduced pressure, and the residue was washed with methanol (50 ml) 4 times and dried to obtain intermediate 2 as yellow solid. Yield: 63 g (percent yield: 66%).

(2) Synthesis of Intermediate 4

Intermediate 2 (5 g, 18.9 mmol) was dissolved in absolute THF, and isopropylmagnesium chloride (9.5 ml, concentration: 2M, solvent: absolute THF) was slowly added thereto at −50° C., and then the resultant mixture was stirred at room temperature for 1 hour. Subsequently, said mixture was cooled to −78° C., and phosphorus trichloride (1.3 g, 9.5 mmol) was slowly added. After that, the mixture was stirred at room temperature overnight, and the resultant reaction product containing intermediate 4 was used for the next reaction without further purification.

(3) Synthesis of Intermediate 8

Compound 5 (1.84 g, 9.5 mmol) shown in the above scheme was dissolved in absolute THF (20 ml), and a solution of n-butyllithium in n-hexane (4.2 ml, 10.5 mol) was slowly added thereto at 0° C. under the nitrogen atmosphere. After the solution was stirred at the same temperature for 30 minutes, the solution was gradually warmed up and stirred at room temperature for 1.5 hours. Subsequently, a solution of intermediate 4 obtained above in THF was added dropwise to said solution at −78° C., and the resultant reaction mixture was stirred at room temperature overnight. After completion of stirring, water was added to the reaction mixture, the mixture was extracted with ethyl acetate, and the organic layer was dried over sodium sulfate. Inorganic salt was filtered off, and the organic layer was concentrated under the reduced pressure. The resultant residue was purified through a silica gel column to obtain the desired intermediate 8 (2.5 g). Similar reaction was carried out by scaling up this synthesis, and finally intermediate 8 (12 g) was obtained.

(4) Synthesis of B-14

Intermediate 8 (12 g) was dissolved in diethyl ether (50 ml), a diethyl ether solution saturated with hydrogen chloride (100 ml) was added thereto at −40° C. After stirring at the same temperature for 1 hour, the solution was gradually warmed up to room temperature and stirred at room temperature for further 1 hour. The reaction mixture was concentrated under the reduced pressure to obtain B-14 hydrochloride as grayish white solid.

The resultant hydrochloride was dissolved in dichloromethane (100 ml), and a saturated sodium hydrogen carbonate aqueous solution (250 ml) was slowly added thereto. After stirring at room temperature for 30 minutes, the mixture was extracted with dichloromethane (150 ml) 3 times. The organic layers were combined, and dried over sodium sulfate. After drying, inorganic salt was filtered off, and the filtrate was concentrated under the reduced pressure. And the residue was washed with petroleum ether (50 ml) twice to obtain the desired ligand B-14 as a grayish white solid. Yield: 6 g.

$^1$HNMR (CDCl$_3$, δ ppm): 7.30-6.39 (m, 9H), 3.46 (s, 12H), 1.31 (s, 9H); $^{31}$PNMR (CDCl$_3$, δ ppm): 62.9 (s).

Synthesis Example 2

Synthesis of Ligand B-7

(1) Synthesis of intermediate B-7__5

[Formula 14]

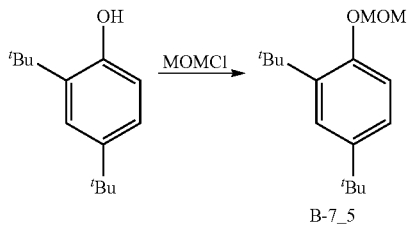

B-7_5

According to the above scheme, intermediate B-7__5 was synthesized. In this scheme, MOM represents methoxymethyl group (hereinafter, same as above).

2,4-Di-t-butylphenol (10 g, 48.5 mmol) was dissolved in THF (100 ml). This solution was added dropwise at 0° C. with stirring to a solution of sodium hydride (2.91 g, 1.5 eq., and dispersion in mineral oil in a concentration of 60%) in THF (200 ml) prepared separately. The solution was gradually warmed up to room temperature and reacted at room temperature for 2 hours. Subsequently, chloromethoxymethane (7.76 g) was added dropwise at 0° C., and the solution was warmed up to room temperature, then reacted at room temperature for 3 hours. The cloudy white solution was extracted with water and ethyl acetate. The organic layer was washed with aqueous KOH solution (1 M, 150 ml) and then water (150 ml), and dried over sodium sulfate. Inorganic salt was filtered off, and the filtrate was concentrated under the reduced pressure, to obtain a pale yellow oil. The resultant oil was purified through a column using petroleum ether/ethyl acetate (40/1) as an eluent, to obtain the desired intermediate B-7__5 (10.5 g).

(2) Synthesis of Intermediate B-7__6

[Formula 15]

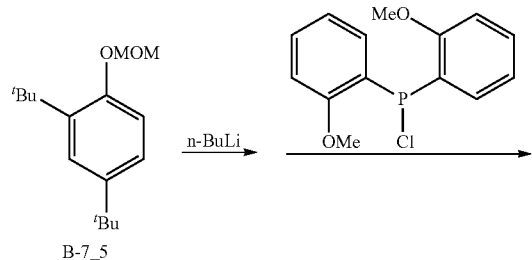

B-7_5

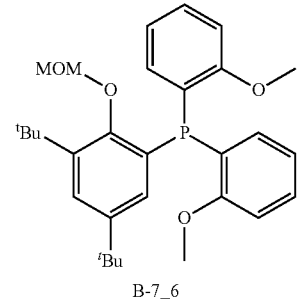

B-7_6

According to the above scheme, intermediate B-7__6 was synthesized.

Intermediate B-7__5 (0.75 g, 3.0 mmol) was dissolved in THF (30 ml), and n-butyllithium (2.5 M, 1.2 ml, 3.0 mmol) was added dropwise thereto at 0° C. under the atmosphere of argon. The solution was gradually warmed up to room temperature, and reacted at room temperature for 3 hours. Subsequently, a solution of bis(2-methoxyphenyl)chlorophosphine (700 mg, 2.50 mmol) dissolved in THF (15 ml) was added dropwise to this reaction mixture at 0° C. The solution was gradually warmed up to room temperature and stirred at room temperature overnight. After completion of stirring, deaerated saturated aqueous ammonium chloride solution (10 ml) was added, and after separating the organic layer, the solution was extracted with diethyl ether, and the organic layer was washed with brine (10 ml), then dried over sodium sulfate to obtain intermediate B-76.

By repeating similar procedures, finally intermediate B-7__6 (8 g) was obtained.

(3) Synthesis of Intermediate B-7_HCl

[Formula 16]

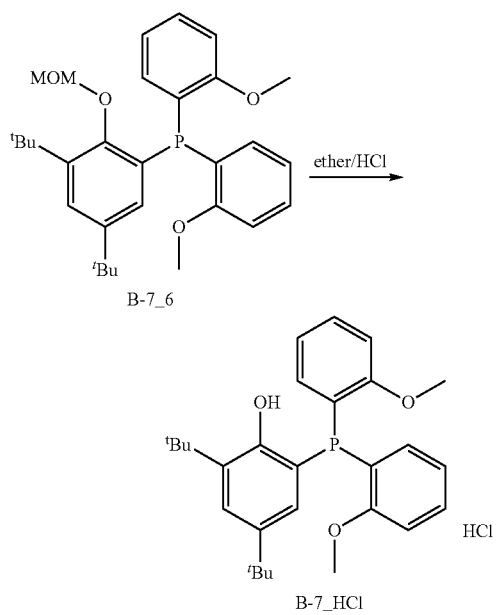

According to the above scheme, intermediate B-7_HCl was synthesized. Intermediate B-7_HCl (8 g) obtained in Synthesis Example 5(2) was dissolved in diethyl ether (500 ml), and hydrogen chloride gas was introduced by bubbling into the solution at −78° C. for 25 minutes. After that, the solution was warmed up to room temperature and stirred at room temperature overnight. After completion of stirring, the solvent was distilled off to obtain B-7_HCl.

(4) Synthesis of Ligand B-7

[Formula 17]

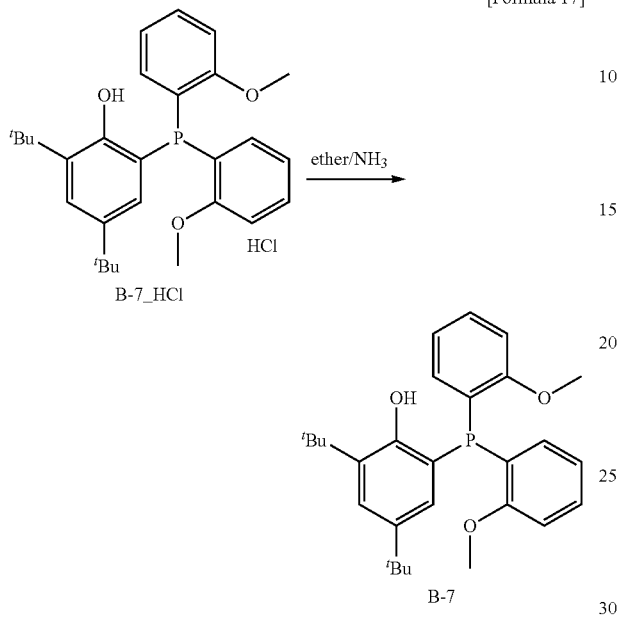

According to the above scheme, ligand B-7 was synthesized.

A part (7.3 g) of intermediate B-7_HCl obtained in Synthesis Example 5(3) was dissolved in diethyl ether (500 ml), and ammonia gas was introduced by bubbling into the solution at −78° C. for 30 minutes. Subsequently, the solution was warmed up to room temperature and stirred at room temperature overnight. After completion of stirring, the solvent was distilled off to obtain crude B-7. After the resultant crude B-7 was dispersed in diethyl ether (10 ml), suspension washing was carried out by adding n-hexane (100 ml). After solid component was removed, the solvent was removed under the reduced pressure to obtain the desired ligand B-7. Yield: 5.2 g.

$^1$HNMR (MeOD, δ ppm): 7.38-6.69 (m, 10H), 3.70 (s, 6H), 1.43 (s, 9H), 1.10 (s, 9H); $^{31}$PNMR (MeOD, δ ppm): 48.2 (s).

Synthesis Example 3

Synthesis of Nickel Complex 1

To a mixture of acyltriphenylphosphoranyl metarene (1.237 g, 4.0 mmol) and bis-1,5-cyclooctadiene nickel (0) (hereinafter, referred to as Ni(COD)$_2$) (1.10 g, 4.0 mmol), toluene (40 ml) was added at room temperature to obtain a yellow suspension. To this suspension, 2,6-lutidine (0.86 g, 8.0 mmol) was added using a syringe. After stirring the resultant mixture at room temperature, the mixture was warmed up to 60° C. with stirring, and reacted at 60° C. for 3.5 hours, to obtain a dark brown solution. The resultant solution was filtered with a cannula, and the resultant dark brawn filtrate was concentrated under the reduced pressure to ¼ of the original volume. To this concentrated solution, n-hexane (about 3 ml) was added dropwise until the liquid became turbid. Subsequently, this turbid liquid was warmed up to 65° C. to obtain a transparent solution. The resultant transparent solution was gradually cooled to room temperature over 2 to 3 hours, and yellow fine crystal was precipitated at around room temperature. The precipitated crystal was kept in the mother liquid overnight. After that, the supernatant was filtered off with a cannula, and the remained solid was washed with n-hexane (3 ml) twice, and the solid was finally dried under the reduced pressure at 6×10$^{-3}$ mbar, to obtain yellow crystal (1.17 g, percent yield: 60.4%).

$^1$HNMR (C$_6$D$_6$, δ ppm): 7.67 (m, 5H), 7.37 (d, 2H), 7.2-7.0 (m, 4H), 6.77 (m, 4H), 6.56 (d, 1H), 6.50 (t, 1H), 6.15 (d, 1H), 4.20 (s, 1H), 3.49 (s, 6H), 2.06 (s, 3H); $^{31}$PNMR (C$_6$D$_6$, δ ppm): 21.78 (s).

[Formula 18]

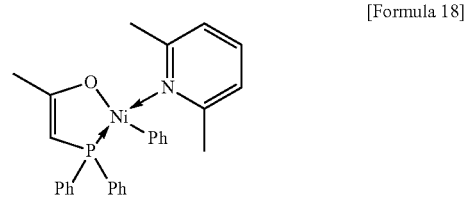

Structure of nickel complex 1

Synthesis Example 4

Synthesis of ligand B-27_DM (1) Synthesis of Intermediate B-27DM__3

According to the following scheme, intermediate B-27DM__3 was synthesized.

A solution of 2,6-dimethoxyiodobenzene (10 g, 37.9 mmol) dissolved in dry THF was added dropwise to isopropylmagnesium chloride (18.9 mmol, 2M THF solution) at −50° C. The resultant mixture was warmed up to room temperature while stirring and stirred at room temperature for 1 hour. Subsequently, the mixture was cooled to −78° C., and phosphorus trichloride (1.6 ml, 18.9 mmol) was slowly added thereto. The resultant mixture was warmed up to room temperature with stirring, and stirred at room temperature for 1 hour. The solvent was removed under the reduced pressure to obtain a solid of B-27DM__3. The solid was dissolved again by adding THF (150 ml) to obtain a solution of B-27DM__3 in THF.

[Formula 19]

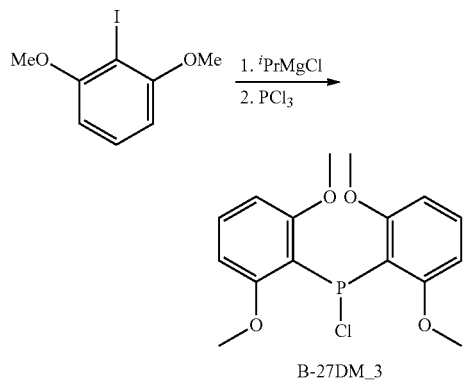

(2) Synthesis of Intermediate B-27DM__5

According to the following scheme, intermediate B-27DM__5 was synthesized.

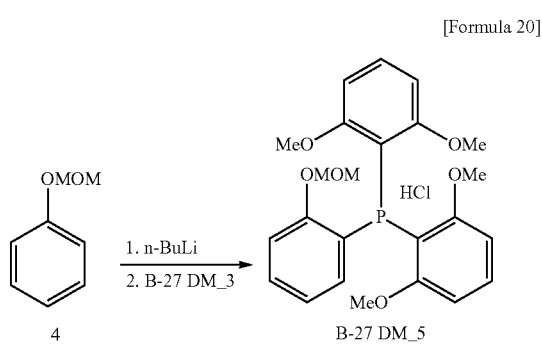

[Formula 20]

Methoxymethylphenol 4 (2.87 g, 20.8 mmol) was dissolved in dry THF (20 ml), and added dropwise to a solution of n-butyllithium (8.3 ml, 20.8 ml) in n-hexane at 0° C. After stirring the resultant mixture at 0° C. for 30 minutes, the mixture was warmed up to room temperature, and stirred at room temperature for 2 hours. To this reaction solution, a solution of B-27DM__3 obtained in Synthesis Example 4 (1) in THF was added at 0° C., and the resultant solution was further stirred at room temperature overnight. The reaction liquid was quenched with water, and THF was removed under the reduced pressure. The resultant mixture was extracted with dichloromethane, and the organic layer was washed with brine. Further, the organic layer was dried by adding sodium sulfate. After sodium sulfate was filtered off, the filtrate was concentrated by removing the solvent under the reduced pressure. The resultant crude product was purified through a silica gel column using dichloromethane as an eluent, and then dichloromethane was removed to obtain B-27DM__5 as a white solid.

(3) Synthesis of Intermediate B-27DM__6

According to the following scheme, intermediate B-27DM__6 was synthesized.

B-27DM__5 (3.2 g, 7.2 mmol) obtained in Synthesis Example 4 (2) was dissolved in dry THF (50 ml). To this solution, n-butyllithium (2.9 ml, 7.2 mmol) was added dropwise at 0° C. The resultant reaction solution was warmed up with stirring, and stirred at room temperature for 2 hours. Subsequently, the solution was cooled to −78° C., and hexafluorobenzene (4 ml, 36 mmol) was slowly added thereto. The solution was warmed up to room temperature with stirring and stirred at room temperature overnight. The reaction was quenched by adding water, and the solvent was removed under the reduced pressure. The solid residue was extracted with dichloromethane, and the organic layer was washed with brine. The organic layer was then dried over sodium sulfate, and after sodium sulfate was filtered off, the solvent was removed under the reduced pressure to concentrate the filtrate. The crude product was purified through a silica gel column using a mixed solvent of petroleum ether/ethyl acetate=7/1 (v/v) as an eluent. After the purification, the solvent was removed to obtain B-27DM__6 (1.2 g).

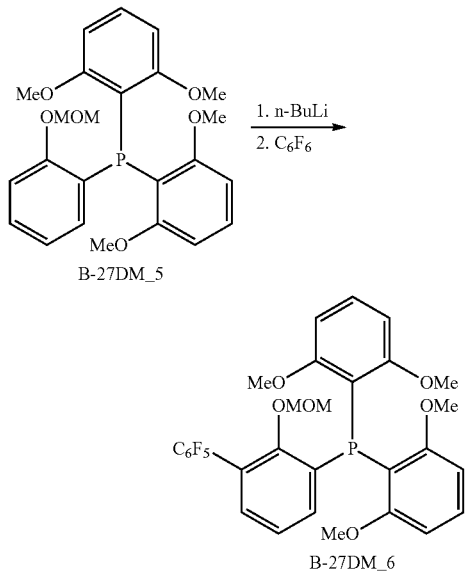

[Formula 21]

(4) Synthesis of B-27DM_HCl

Same procedures were carried out as in Synthesis Example 4 (1) to (3) to obtain B-27DM__6 (6.7 g). Subsequently, according to the following scheme, intermediate B-27DM-_HCl was synthesized.

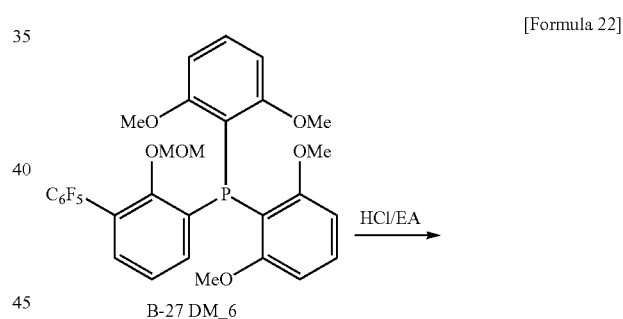

[Formula 22]

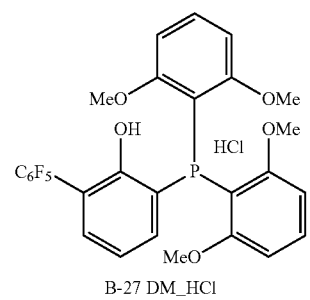

B-27DM__6 (5.5 g) was added to hydrogen chloride (concentration=4 M, a solution in ethyl acetate, 100 ml) at 0° C. The resultant mixture was gradually warmed up to room temperature, and stirred at room temperature for 1.5 hours. Ethyl acetate was removed under the reduced pressure, to obtain B-27DM_HCl as a white solid.

(5) Synthesis of Ligand B-27DM

According to the following scheme, ligand B-27DM was synthesized.

[Formula 23]

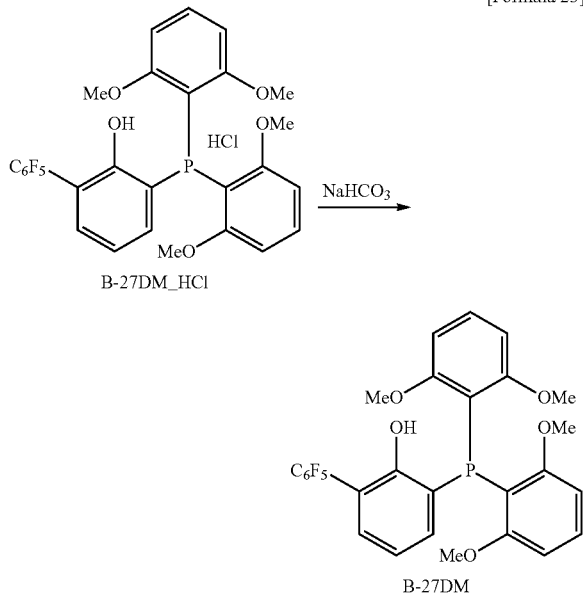

A mixture of B-27DM_HCl (5.0 g), saturated sodium hydrogen carbonate aqueous solution (200 ml) and ethyl acetate (100 ml) was stirred at room temperature under the argon atmosphere for 2 hours. The desired compound was extracted with ethyl acetate from the resultant reaction mixture, and the organic layer was washed with brine. After drying the organic layer on sodium sulfate, sodium sulfate was filtered off, and the solvent was removed under the reduced pressure. The crude product was washed with a mixed solvent of petroleum ether and ethyl acetate, to obtain the desired B-27DM as a white solid. Yield: 2.8 g.

$^1$HNMR (CDCl$_3$, δ ppm): 7.70-7.76 (m, 1H), 7.29 (s, broad, 1H), 7.26-7.20 (m, 2H), 7.10 (d, 1H), 6.88 (t, 1H), 6.50 (m, 4H), 3.55 (s, 12H); $^{31}$PNMR (CDCl$_3$, δ ppm): −60.4 (s).

Synthesis Example 5

Synthesis of Ligand B-30

(1) Synthesis of Intermediate B-30_3

According to the following scheme, intermediate B-30_3 was synthesized.

[Formula 24]

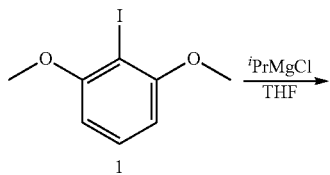

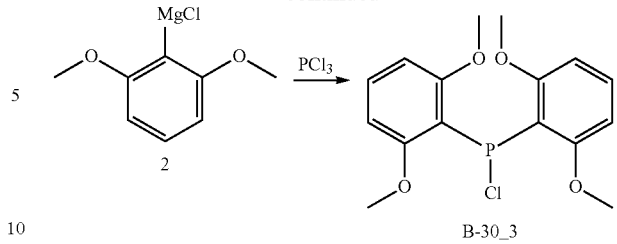

2,6-Dimethoxyiodobenzene (5.2 g, 20 mmol) was dissolved in dry THF, and isopropylmagnesium chloride (10 ml, 2M, THF solution) was added dropwise thereto at −50° C. The resultant reaction mixture was warmed up with stirring, and stirred at room temperature for 1 hour. The reaction mixture was cooled to −78° C., and phosphorus trichloride (1.37 g, 10 mmol) was slowly added thereto. The mixture was gradually warmed up to room temperature to obtain a solution of B-30_3 in THF. The resultant solution of B-30_3 in THF was used for the next reaction without purification.

(2) Synthesis of Intermediate B-30_8

According to the following scheme, intermediate B-30_8 was synthesized.

[Formula 25]

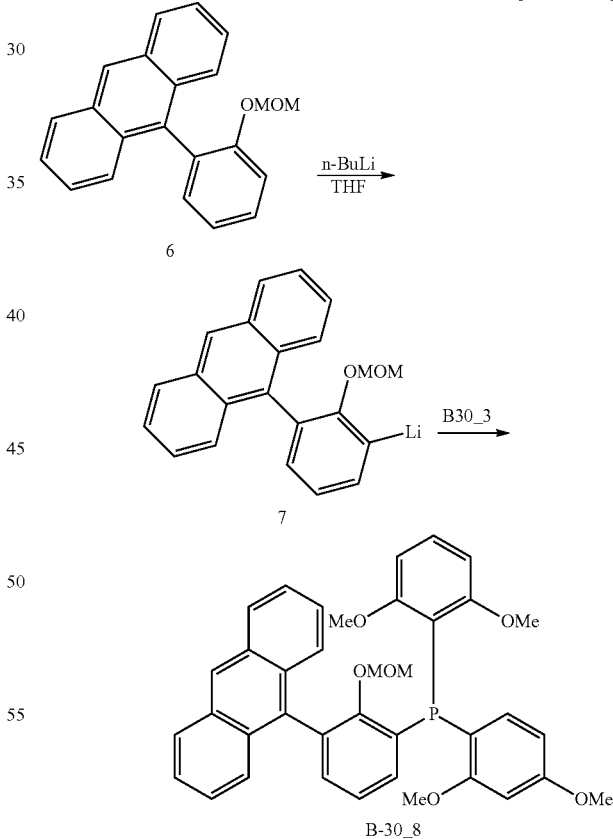

Compound 6 (3.14 g, 10 mmol) was dissolved in dry THF (100 ml), and to the resultant solution, n-butyllithium solution (4 ml, 10 mmol) was added dropwise at 0° C. After stirring at 0° C. for 1 hour, the solution was warmed up to room temperature with stirring, and then stirred at room temperature for further 1 hour. The solution was cooled to −30°

C., and a solution of B-30_3 obtained in Synthesis Example 5 (1) in THF was added dropwise thereto at the same temperature. The solution was gradually warmed up with stirring, and stirred at room temperature overnight. The reaction was quenched with water, and THF was removed under the reduced pressure. The mixture was extracted with ethyl acetate, and the organic layer was washed with brine. After drying the organic layer on sodium sulfate, sodium sulfate was filtered off, and the solvent was distilled off under the reduced pressure to concentrate. The resultant crude product was purified through a silica gel column using petroleum ether/ethyl acetate (10/1, v/v) as an eluent, to obtain B-30_8 (1.34 g).

(3) Synthesis of Ligand B-30

According to the following scheme, ligand B-30 was synthesized.

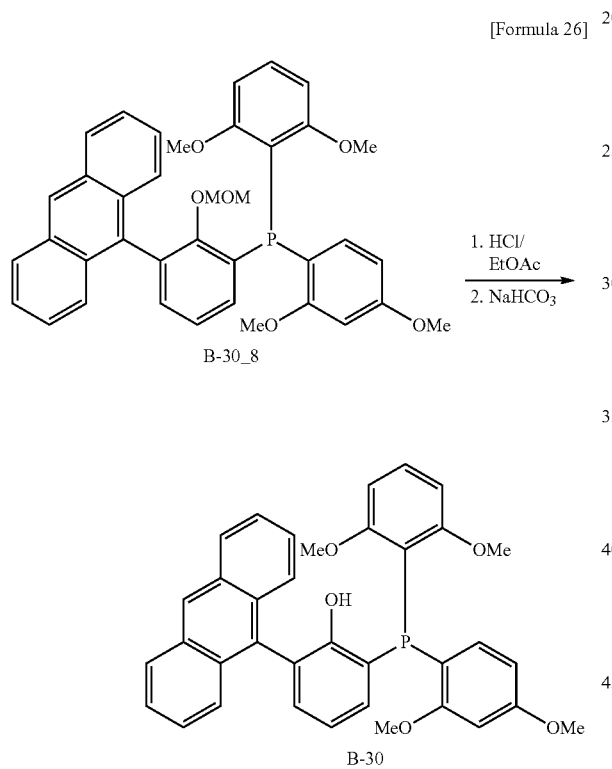

[Formula 26]

Ethyl acetate (50 ml) was cooled to −78° C., and hydrogen chloride gas was blown therein at the same temperature. Subsequently, B-30_8 (1.34 g) obtained in Synthesis Example 5 (2) was added thereto. The resultant mixture was gradually warmed up to room temperature with stirring, and stirred at room temperature for 1.5 hours. Ethyl acetate was removed under the reduced pressure, and the resultant crude product was neutralized with saturated sodium hydrogen carbonate aqueous solution. Yellow solid of B-30 was obtained. Yield: 0.9 g.

$^1$HNMR (CDCl$_3$, δ ppm): 8.37 (s, 1H), 7.92 (d, 2H), 7.59 (m, 3H), 7.33 (m, 2H), 7.17 (m, 2H), 7.12 (t, 2H), 7.10 (d, 1H), 6.89 (t, 1H), 6.39 (m, 4H), 6.35 (s, 1H), 3.52 (s, 12H); $^{31}$PNMR (CDCl$_3$, δ ppm): −60.1 (s).

Synthesis Example 6

Synthesis of ligand B-56DM (1) Synthesis of intermediate B-56DM_3

According to the following scheme, intermediate B-56DM_3 was synthesized.

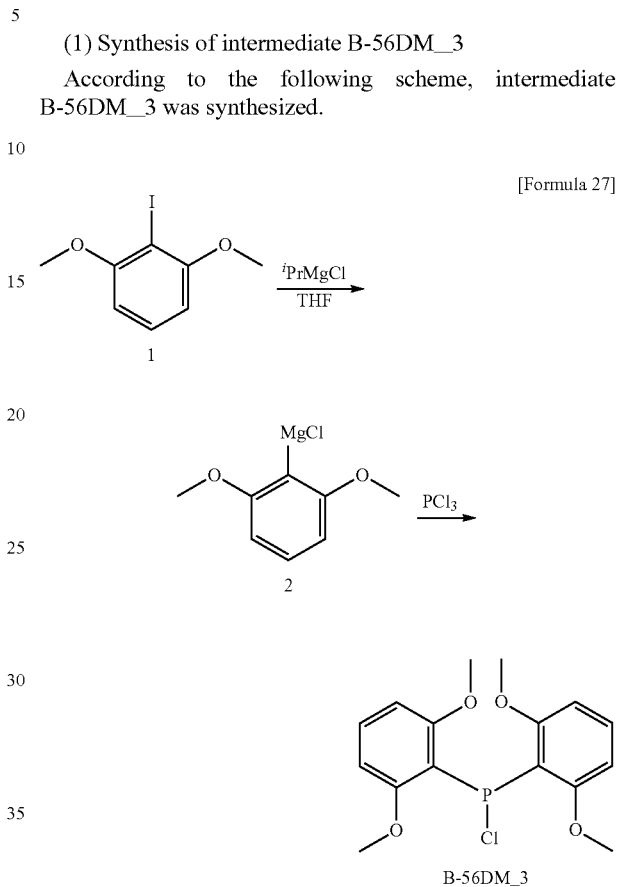

[Formula 27]

2,6-Dimethoxyiodobenzene (10 g, 37.9 mmol) was dissolved in dry THF, and isopropylmagnesium chloride (18.9 ml, 2M, THF solution) was added dropwise thereto at −50° C. The resultant reaction mixture was warmed up with stirring, and stirred at room temperature for 1 hour. The reaction mixture was cooled to −78° C., and phosphorus trichloride (1.6 ml, 18.9 mmol) was slowly added thereto. The mixture was gradually warmed up to room temperature with stirring, and stirred at room temperature for 1 hour. The solvent was removed under the reduced pressure, to obtain a solid of B-56DM_3. Subsequently, THF (150 ml) was added to obtain a solution of B-56DM_3 in THF.

(2) Synthesis of Intermediate B-56DM_6

According to the following scheme, intermediate B-56DM_6 was synthesized.

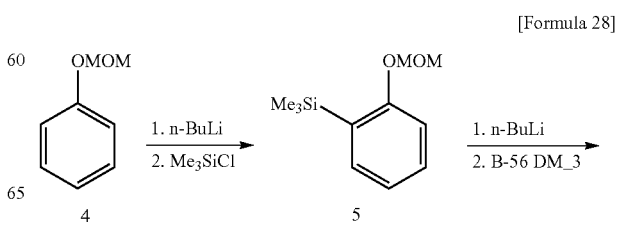

[Formula 28]

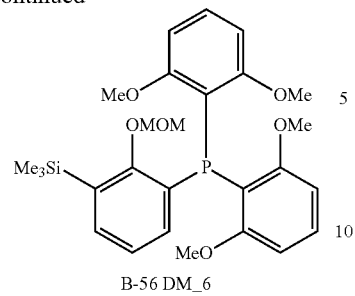

B-56 DM_6

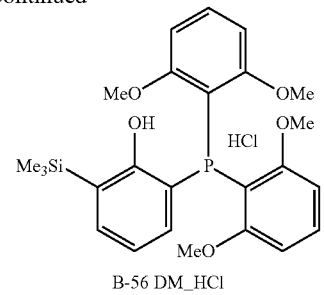

B-56 DM_HCl

Compound 4 (3.16 g, 22.7 mmol) was dissolved in dry THF (50 ml), and the solution was cooled to 0° C. A solution of n-butyllithium in n-hexane (9.1 ml, 22.7 mmol) was added dropwise thereto at 0° C., and the solution was stirred at 0° C. for 30 minutes. The solution was warmed up to room temperature with stirring, and stirred at room temperature for further 2 hours. The solution was cooled to 0° C., and after adding trimethylsilyl chloride (2.90 ml, 22.7 mmol), the solution was stirred at room temperature for 1 hour. The solution was cooled again to 0° C., and a solution of n-butyllithium in n-hexane (9.1 ml, 22.7 mmol) was added dropwise thereto at 0° C. The mixture was warmed up to room temperature with stirring, and stirred at room temperature for 2 hours. The mixture was cooled again to 0° C., and a solution of B-56 DB_3 synthesized in Synthesis Example 6 (1) in THF was added thereto at 0° C., and the resultant reaction mixture was stirred at room temperature overnight. The reaction was quenched with a 10% sodium hydroxide aqueous solution, and then THF was removed under the reduced pressure. The mixture was extracted with ethyl acetate, and the organic layer was washed with brine. The organic layer was dried on sodium sulfate, and after sodium sulfate was filtered off, the solvent was distilled off under the reduced pressure to concentrate. The crude product was purified through a silica gel column using petroleum ether/ethyl acetate (10/1, v/v) as an eluent, to obtain B-56DM_6 (3.6 g) as a white solid.

(3) Synthesis of Intermediate B-56DM_HCl

Procedures were repeated as in Synthesis Example 6 (1) and (2) to obtain B-56DM_6 (7.4 g). Subsequently, according to the following scheme, intermediate B-56DM_HCl was synthesized.

[Formula 29]

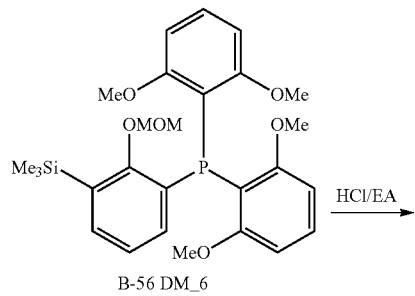

A solution of hydrogen chloride in ethyl acetate (concentration=2 M) was prepared. To this hydrogen chloride solution, B-56DM_6 (7.4 g) was added at 0° C. The resultant mixture was gradually warmed up to room temperature, and stirred at room temperature for 1.5 hours. Ethyl acetate was removed under the reduced pressure to obtain B-56DM_HCl as a white solid.

(4) Synthesis of Ligand B-56DM

According to the following scheme, ligand B-56DM was synthesized.

[Formula 30]

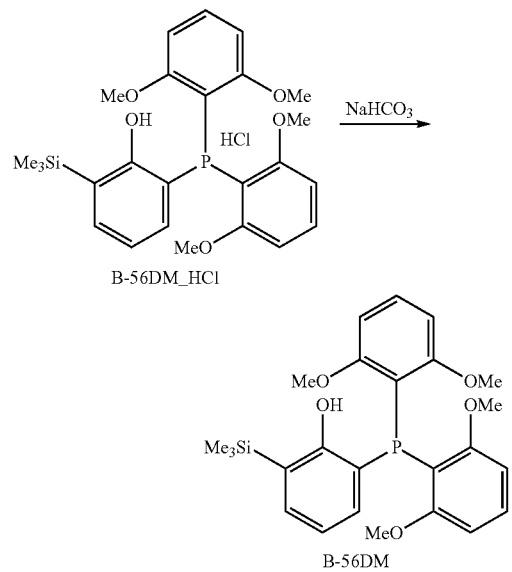

A mixture of B-56DM_HCl (7.2 g), saturated sodium hydrogen carbonate aqueous solution (200 ml), and ethyl acetate (150 ml) was stirred for 2 hours under the argon atmosphere. The mixture was extracted with ethyl acetate, and the organic layer was washed with brine. The organic layer was dried on sodium sulfate, and after filtering off sodium sulfate, the solvent was removed under the reduced pressure to concentrate. The resultant crude product was further dried for 3 hours under the reduced pressure, to obtain the desired B-56DM. Yield: 6.3 g.

$^1$HNMR (CDCl$_3$, δ ppm): 7.58 (m, 1H), 7.29 (m, 1H), 7.22 (m, 2H), 6.99 (s, broad, 1H), 6.79 (t, 1H), 6.50 (m, 4H), 3.56 (s, 12H), 0.27 (s, 9H); $^{31}$PNMR (CDCl$_3$, δ ppm): −61.6 (s).

Examples 1 to 24

Homopolymerization of ethylene and copolymerization of ethylene/acrylate using ligand B-14 obtained in Synthesis Example 1

(1) Formation of Complex

All of the following operations were conducted under the atmosphere of high-purity argon. Hereinafter, bis-1,5-cyclooctadiene nickel (0) is referred to as Ni(COD)$_2$.

Firstly, B-14 (10.8 mg) obtained in Synthesis Example 1 was weighed and charged into a 4 ml vial with screw cap. Next, Ni(COD)$_2$ (20 mg) was weighed and charged into a 8 ml vial, and dissolved in toluene (7.22 ml) to prepare a solution of 10 mM Ni(COD)$_2$ in toluene. The resultant solution was yellow and transparent. The resultant Ni(COD)$_2$ solution in toluene (2.36 ml) was added to the vial having B-14, and after sealed hermetically with screw cap, the mixture was stirred for 30 seconds to obtain a solution. After that, color of the solution gradually changed from dark yellow to red, and no precipitation was observed. After the solution was left at room temperature for 3 hours, a part of the resultant solution (0.5 ml) was separated into a 2 ml vial, and diluted with toluene (1.5 ml), to obtain a 2.5 mM solution of a reaction product of B-14 and Ni(COD)$_2$. The concentration of the reaction product was calculated assuming that B-14 and Ni(COD)$_2$ reacted in a molar ratio of 1:1 to form a nickel complex.

(2) Homopolymerization of ethylene and copolymerization of ethylene/acrylate

Dry toluene (4.2 ml) and a predetermined amount of acrylate were charged into an autoclave having an inner volume of about 1 ml and equipped with an agitating blade and an inner cylinder. It should be noted that, when homopolymerization of ethylene was carried out, acrylate was not charged. After the autoclave was warmed up to a predetermined temperature with stirring, ethylene was supplied to the autoclave, and temperature and pressure were adjusted to the predetermined conditions. After completion of adjustment, a predetermined amount of the reaction product obtained in the above (1) was supplied to initiate copolymerization. After the polymerization was carried out for a predetermined time, carbon monoxide was blown therein. After removing unreacted gas, the inner cylinder was taken out, and the solvent and the unreacted comonomer were removed under the reduced pressure, and dried until constant weight was obtained.

Kinds and amounts of the comonomers used for the copolymerization were described in Table 1. Comonomers were used after purifying using a column packed with Aldrich Inhibitor Remover produced by Aldrich Co. at room temperature under the atmosphere of high-purity argon. In addition, amounts of toluene used for the polymerization, polymerization temperatures, and internal pressures of the autoclave during the polymerization were also described in Table 1. In Table 1, tBA represents t-butyl acrylate. In addition, activity Vp represents copolymer yield (kg) per 1 mol of the complex used for the polymerization and per 1 hour of polymerization time. It should be noted that, Vp was calculated assuming that B-14 and (COD)$_2$ reacted in a molar ratio of 1:1 to form a nickel complex. Measurement results on GPC and DSC for the obtained polymers were also described in Table 1.

Comparative Examples 1 to 21

Homopolymerization of Ethylene and Copolymerization of Ethylene/Acrylate Using B-7

Polymerization was carried out in a same way as in Examples 1 to 24, except that B-7 obtained in Synthesis Example 2 was used as a ligand in an amount of 10.7 mg. Results are shown in Table 2. Items described in Table 2 are also same as in Table 1.

Comparative Examples 22 to 33

Homopolymerization of Ethylene and Copolymerization of Ethylene/Acrylate Using Nickel Complex 1

Polymerization was carried out in the same way as in Examples 1 to 24, except that nickel complex 1 obtained in Synthesis Example 3 was used instead of the contact product of a ligand and a transition metal complex component (C). Results are shown in Table 3. Items described in Table 3 are also same as in Table 1.

Example 25

Isolation and X-Ray Crystal Structure Analysis of the Complex Obtained by the Reaction Between Ligand B-14 Obtained in Synthesis Example 1 and Ni(Cod)$_2$ Firstly, B-14 and Ni(COD)$_2$ were reacted in the same way as in (1) Formation of complex in Examples 1 to 24, to obtain a solution of nickel complex of B-14 in toluene. After the solvent was distilled off under the reduced pressure, the complex was dissolved again using a mixed solvent composed of toluene/n-pentane (1/1, v/v) at room temperature. After the solution was filtered, the filtrate was transferred to a Schlenk tube and cooled to −20° C., and then n-pentane was poured gently to the top of the solution to form two layers. When the Schlenk tube was left in a freezer at −20° C. for 3 days, n-pentane in the upper layer diffused gradually, and finally a homogeneous solution was obtained. In the resultant homogeneous solution, growth of single crystal of the B-14/nickel complex was observed.

A single crystal having dimensions of about 0.5×0.4×0.35 mm was selected from the obtained single crystals, and set in a glass capillary, and said capillary was mounted on SMART 100 CCD diffractometer manufactured by Bruker equipped with a pedestal of triaxial goniometer and 1K CCD detector, at −170° C. The single crystal was set 50 mm away from the diffractometer. Diffraction intensity measurement was carried out using Mo—Kα line monochromatized by graphite. Lattice constant was determined first, and reflection data of 1,800 frames were obtained using program SAINT. For the obtained data, Lorentz correction, absorption correction and sample decay correction were made.

Unit lattice of the obtained single crystal was triclinic, and space group was P-1. Structure was determined by direct method using program SHELX97. For F$^2$ of reflection observed by SHELX97, refinement was carried out by the full matrix least square method. It should be noted that, for all atoms other than hydrogen, structure refinement was carried out by anisotropic temperature factor, and positions of hydrogen atoms were determined by calculation and structure refinement was carried out by isotropic temperature factor. Data converged with R$^2$ (I>2σ(I))=0.1727.

As a result of the X-ray crystal structure analysis, it became apparent that the obtained complex had a chemical formula of C$_{34}$H$_{43}$O$_5$PNi, and slightly hindered planar four-coordinate structure as shown in the following ORTEP drawing. It should be noted that, the distance between nickel and oxygen in an axial position to the plane made by Ni and the ligand among four methoxy groups was 2.95 Å.

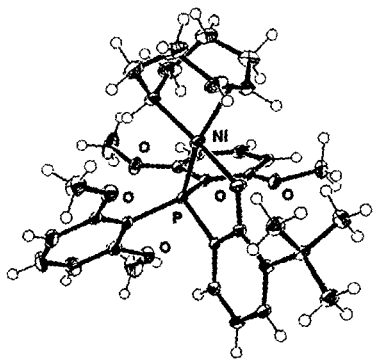

ORTEP drawing of the complex obtained by the reaction between B-14 and Ni(COD)$_2$

Examples 26 to 29

Homopolymerization of Ethylene Using Ligand B-27DM Obtained in Synthesis Example 4

(1) Formation of Complex

A complex was formed in the same way as in Examples 1 to 24 except that B-27DM (13.4 mg) obtained in Synthesis Example 4 was used as a ligand.

(2) Homopolymerization of Ethylene

Homopolymerization of ethylene was carried out in the same way as in Examples 1 to 24 except that the compounds obtained in the above (1) were used as a complex. Results are shown in Table 4.

Examples 30 to 33

Homopolymerization of Ethylene Using Ligand B-30 obtained in Synthesis Example 5

(1) Formation of Complex

A complex was formed in the same way as in Examples 1 to 24 except that B-30 (13.7 mg) obtained in Synthesis Example 4 was used as a ligand.

(2) Homopolymerization of Ethylene

Homopolymerization of ethylene was carried out in the same way as in Examples 1 to 24 except that the compounds obtained in the above (1) were used as a complex. Results are shown in Table 5.

Examples 34 to 65

Homopolymerization of ethylene and copolymerization of ethylene/acrylate using ligand B-14 obtained in Synthesis Example 1

(1) Formation of Complex

The complex was formed in the same way as in Examples 1 to 24.

(2) Homopolymerization of Ethylene and Copolymerization of Ethylene/Acrylate

Homopolymerization of ethylene and copolymerization of ethylene/acrylate were carried out in the same way as in Examples 1 to 24 except that Lewis bases were added in the autoclave as an additive. Results are shown in Table 6. In Table 6, DMAP represents N,N-dimethylaminopyridine, 2,2'-BiPy represents 2,2'-bipyridine, and NMI represents N-methylimidazole.

Examples 66 to 87

Homopolymerization of ethylene and copolymerization of ethylene/acrylate using ligand B-14 obtained in Synthesis Example 1 and B-30 obtained in Synthesis Example 4.

(1) Formation of Complex

The complex was formed in the same way as in Examples 1 to 24.

(2) Homopolymerization of Ethylene and Copolymerization of Ethylene/Acrylate

Homopolymerization of ethylene and copolymerization of ethylene/acrylate were carried out in the same way as in Examples 1 to 24 except that an autoclave having a volume of 2 liter was used. Results are shown in Table 7.

Examples 88 to 91

Homopolymerization of Ethylene Using Ligand B-56DM Obtained in Synthesis Example 6

(1) Formation of Complex

The complex was formed in the same way as in Examples 1 to 24 except that B-56 DB (11.2 mg) obtained in Synthesis Example 6 was used as a ligand.

(2) Homopolymerization of Ethylene

Homopolymerization of ethylene was carried out in the same way as in Examples 1 to 24, except that the compound obtained in the above (1) was used as a complex. Results are shown in Table 8.

TABLE 1

| Example | Ligand | Solvent | Amount of complex (μmol) | Internal pressure (MPa) | Kind/amount of comonomer (μmol) | Polymerization time (sec) | Polymerization temperature (°C.) | Activity Vp (kg/mol/h) | Tm (°C.) | Tc (°C.) | Mw | Mn | Mw/Mn |
|---|---|---|---|---|---|---|---|---|---|---|---|---|---|
| 1 | B-14 | Toluene (4.2 ml) | 0.05 | 2.8 | 0 | 3601 | 70 | 142 | n/a | n/a | 262000 | 164000 | 1.6 |
| 2 | B-14 | Toluene (4.2 ml) | 0.20 | 2.8 | tBA (50) | 3602 | 70 | 47 | 125 | 114 | 185500 | 74000 | 2.5 |
| 3 | B-14 | Toluene (4.2 ml) | 0.20 | 2.8 | tBA (100) | 3601 | 70 | 27 | n/a | n/a | 122500 | 94000 | 1.3 |
| 4 | B-14 | Toluene (4.2 ml) | 0.20 | 2.8 | tBA (200) | 3600 | 70 | 14 | n/a | n/a | n/a | n/a | n/a |
| 5 | B-14 | Toluene (4.2 ml) | 0.20 | 2.8 | 0 | 306 | 70 | 21412 | n/a | n/a | n/a | n/a | n/a |
| 6 | B-14 | Toluene (4.2 ml) | 0.80 | 2.8 | tBA (200) | 3601 | 70 | 66 | 116 | 103 | 112500 | 63000 | 1.8 |
| 7 | B-14 | Toluene (4.2 ml) | 0.80 | 2.8 | tBA (400) | 3601 | 70 | 35 | 106 | 90 | 59500 | 37000 | 1.6 |
| 8 | B-14 | Toluene (4.2 ml) | 0.80 | 2.8 | tBA (800) | 3601 | 70 | 18 | 91 | 73 | 42500 | 26500 | 1.6 |
| 9 | B-14 | Toluene (4.2 ml) | 0.10 | 2.8 | 0 | 3602 | 50 | 93 | n/a | n/a | 340000 | 154500 | 2.2 |
| 10 | B-14 | Toluene (4.2 ml) | 0.30 | 2.8 | tBA (50) | 3600 | 50 | 37 | 127 | 115 | 188000 | 110500 | 1.7 |
| 11 | B-14 | Toluene (4.2 ml) | 0.30 | 2.8 | tBA (100) | 3602 | 50 | 21 | n/a | n/a | 51500 | 15000 | 3.4 |
| 12 | B-14 | Toluene (4.2 ml) | 0.30 | 2.8 | tBA (200) | 3601 | 50 | 7 | n/a | n/a | n/a | n/a | n/a |
| 13 | B-14 | Toluene (4.2 ml) | 0.15 | 2.8 | 0 | 3164 | 50 | 164 | 143 | 121 | n/a | n/a | n/a |
| 14 | B-14 | Toluene (4.2 ml) | 0.80 | 2.8 | tBA (200) | 3601 | 50 | 19 | 118 | 107 | 205500 | 35000 | 5.9 |
| 15 | B-14 | Toluene (4.2 ml) | 0.80 | 2.8 | tBA (400) | 3601 | 50 | 19 | 108 | 97 | 58000 | 34000 | 1.7 |

TABLE 1-continued

| Example | Ligand | Solvent | Amount of complex (μmol) | Internal pressure (MPa) | Kind/amount of comonomer (μmol) | Polymerization time (sec) | Polymerization temperature (° C.) | Activity Vp (kg/mol/h) | Tm (° C.) | Tc (° C.) | Mw | Mn | Mw/Mn |
|---|---|---|---|---|---|---|---|---|---|---|---|---|---|
| 16 | B-14 | Toluene (4.2 ml) | 0.80 | 2.8 | tBA (800) | 3601 | 50 | 9 | n/a | n/a | 43500 | 31000 | 1.4 |
| 17 | B-14 | Toluene (4.2 ml) | 0.15 | 2.8 | 0 | 154 | 100 | 39366 | n/a | n/a | 39000 | 21500 | 1.8 |
| 18 | B-14 | Toluene (4.2 ml) | 0.30 | 2.8 | tBA (50) | 3602 | 100 | 110 | 125 | 113 | n/a | n/a | n/a |
| 19 | B-14 | Toluene (4.2 ml) | 0.40 | 2.8 | tBA (100) | 3602 | 100 | 108 | 120 | 109 | 62500 | 39000 | 1.6 |
| 20 | B-14 | Toluene (4.2 ml) | 0.40 | 2.8 | tBA (200) | 3602 | 100 | 52 | n/a | n/a | 53000 | 38000 | 1.4 |
| 21 | B-14 | Toluene (4.2 ml) | 0.20 | 2.8 | 0 | 86 | 100 | 45335 | 125 | 113 | 18500 | 7000 | 2.7 |
| 22 | B-14 | Toluene (4.2 ml) | 0.80 | 2.8 | tBA (200) | 3602 | 100 | 57 | 115 | 103 | 60500 | 43000 | 1.4 |
| 23 | B-14 | Toluene (4.2 ml) | 0.80 | 2.8 | tBA (400) | 3600 | 100 | 23 | 104 | 90 | 41000 | 27000 | 1.5 |
| 24 | B-14 | Toluene (4.2 ml) | 0.80 | 2.8 | tBA (800) | 3602 | 100 | 16 | n/a | n/a | 32500 | 23000 | 1.4 |

TABLE 2

| Comparative Example | Ligand | Solvent | Amount of complex (μmol) | Internal pressure (MPa) | Kind/amount of comonomer (μmol) | Polymerization time (sec) | Polymerization temperature (° C.) | Activity Vp (kg/mol/h) | Tm (° C.) | Tc (° C.) | Mw | Mn | Mw/Mn |
|---|---|---|---|---|---|---|---|---|---|---|---|---|---|
| 1 | B-7 | Toluene (4.2 ml) | 0.30 | 2.8 | tBA (50) | 2860 | 70 | 183 | 124 | 115 | 6500 | 3600 | 1.8 |
| 2 | B-7 | Toluene (4.2 ml) | 0.30 | 2.8 | tBA (100) | 3500 | 70 | 61 | 123 | 115 | 5000 | 3100 | 1.6 |
| 3 | B-7 | Toluene (4.2 ml) | 0.30 | 2.8 | tBA (200) | 3601 | 70 | 27 | n/a | n/a | 5000 | 3100 | 1.6 |
| 4 | B-7 | Toluene (4.2 ml) | 0.80 | 2.8 | tBA (200) | 1317 | 70 | 378 | 120 | 111 | 5000 | 3300 | 1.5 |
| 5 | B-7 | Toluene (4.2 ml) | 0.80 | 2.8 | tBA (400) | 1898 | 70 | 123 | 114 | 108 | 4500 | 2500 | 1.8 |
| 6 | B-7 | Toluene (4.2 ml) | 0.80 | 2.8 | tBA (800) | 3600 | 70 | 59 | 105 | 103 | 4000 | 2500 | 1.6 |
| 7 | B-7 | Toluene (4.2 ml) | 0.80 | 2.8 | tBA (200) | 3600 | 50 | 99 | 122 | 114 | 8000 | 5000 | 1.6 |
| 8 | B-7 | Toluene (4.2 ml) | 0.80 | 2.8 | tBA (400) | 3602 | 50 | 53 | 119 | 111 | 5000 | 2900 | 1.7 |
| 9 | B-7 | Toluene (4.2 ml) | 0.80 | 2.8 | tBA (800) | 3602 | 50 | 29 | 108 | 107 | 3500 | 2200 | 1.6 |
| 10 | B-7 | Toluene (4.2 ml) | 0.30 | 2.8 | tBA (50) | 673 | 100 | 2796 | n/a | n/a | 4000 | 2700 | 1.5 |
| 11 | B-7 | Toluene (4.2 ml) | 0.30 | 2.8 | tBA (100) | 526 | 100 | 2794 | 120 | 109 | 4000 | 2900 | 1.4 |
| 12 | B-7 | Toluene (4.2 ml) | 0.30 | 2.8 | tBA (200) | 2279 | 100 | 400 | n/a | n/a | 3500 | 2500 | 1.4 |
| 13 | B-7 | Toluene (4.2 ml) | 0.80 | 2.8 | tBA (200) | 811 | 100 | 873 | 117 | 107 | 3500 | 2500 | 1.4 |
| 14 | B-7 | Toluene (4.2 ml) | 0.80 | 2.8 | tBA (400) | 3602 | 100 | 37 | n/a | n/a | 2500 | 1800 | 1.4 |
| 15 | B-7 | Toluene (4.2 ml) | 0.80 | 2.8 | tBA (800) | 3601 | 100 | 57 | n/a | 97 | 3000 | 2100 | 1.4 |
| 16 | B-7 | Toluene (4.2 ml) | 0.10 | 2.8 | 0 | 3468 | 70 | 176 | n/a | n/a | 2500 | 1800 | 1.4 |
| 17 | B-7 | Toluene (4.2 ml) | 0.20 | 2.8 | 0 | 60 | 70 | 82200 | n/a | n/a | 2500 | 1900 | 1.3 |
| 18 | B-7 | Toluene (4.2 ml) | 0.05 | 2.8 | 0 | 3601 | 50 | 32 | n/a | n/a | 2500 | 1900 | 1.3 |
| 19 | B-7 | Toluene (4.2 ml) | 0.20 | 2.8 | 0 | 3602 | 50 | 71 | 128 | 117 | n/a | n/a | n/a |
| 20 | B-7 | Toluene (4.2 ml) | 0.15 | 2.8 | 0 | 2028 | 100 | 1428 | 122 | 113 | n/a | n/a | n/a |
| 21 | B-7 | Toluene (4.2 ml) | 0.20 | 2.8 | 0 | 977 | 100 | 2563 | n/a | n/a | n/a | n/a | n/a |

TABLE 3

| Comparative Example | Ligand | Solvent | Amount of complex (μmol) | Internal pressure (MPa) | Kind/amount of comonomer (μmol) | Polymerization time (sec) | Polymerization temperature (° C.) | Activity Vp (kg/mol/h) | Tm (° C.) | Tc (° C.) | Mw | Mn | Mw/Mn |
|---|---|---|---|---|---|---|---|---|---|---|---|---|---|
| 22 | 1 | Toluene (4.2 ml) | 0.10 | 2.8 | 0 | 3600 | 70 | 444 | 123 | 112 | 4000 | 2500 | 1.6 |
| 23 | 1 | Toluene (4.2 ml) | 0.40 | 2.8 | tBA (200) | 3601 | 70 | 194 | 117 | 108 | 2500 | 1700 | 1.5 |
| 24 | 1 | Toluene (4.2 ml) | 0.60 | 2.8 | tBA (400) | 3602 | 70 | 143 | n/a | n/a | 2500 | 1700 | 1.5 |
| 25 | 1 | Toluene (4.2 ml) | 1.00 | 2.8 | tBA (800) | 3601 | 70 | 54 | 104 | 96 | 1000 | 800 | 1.3 |
| 26 | 1 | Toluene (4.2 ml) | 0.10 | 2.8 | 0 | 3600 | 70 | 92 | n/a | n/a | n/a | n/a | n/a |
| 27 | 1 | Toluene (4.2 ml) | 0.40 | 2.8 | tBA (200) | 1020 | 70 | 310 | 117 | 107 | 2500 | 1800 | 1.4 |
| 28 | 1 | Toluene (4.2 ml) | 0.50 | 2.8 | tBA (400) | 3601 | 70 | 117 | 112 | 103 | 2000 | 1400 | 1.4 |
| 29 | 1 | Toluene (4.2 ml) | 1.00 | 2.8 | tBA (800) | 1385 | 70 | 80 | 104 | 95 | 1000 | 800 | 1.3 |
| 30 | 1 | Toluene (4.2 ml) | 0.10 | 2.8 | 0 | 3602 | 70 | 361 | 122 | 112 | 4000 | 2700 | 1.5 |
| 31 | 1 | Toluene (4.2 ml) | 0.40 | 2.8 | tBA (200) | 3602 | 70 | 224 | 117 | 108 | 2500 | 1700 | 1.5 |
| 32 | 1 | Toluene (4.2 ml) | 0.50 | 2.8 | tBA (400) | 3602 | 70 | 128 | 112 | 104 | 2000 | 1400 | 1.4 |
| 33 | 1 | Toluene (4.2 ml) | 0.80 | 2.8 | tBA (800) | 3600 | 70 | 69 | 103 | 95 | 1000 | 800 | 1.3 |

TABLE 4

| Example | Ligand | Solvent | Amount of complex (μmol) | Internal pressure (MPa) | Kind/amount of comonomer (μmol) | Polymerization time (sec) | Polymerization temperature (° C.) | Activity Vp (kg/mol/h) | Tm (° C.) | Tc (° C.) | Mw | Mn | Mw/Mn |
|---|---|---|---|---|---|---|---|---|---|---|---|---|---|
| 26 | B-27DM | Toluene (4.2 ml) | 5.0 | 0.3 | 0 | 3600 | 50 | 43 | n/a | n/a | n/a | n/a | n/a |
| 27 | B-27DM | Toluene (4.2 ml) | 5.0 | 0.7 | 0 | 3600 | 50 | 86 | n/a | n/a | n/a | n/a | n/a |

TABLE 4-continued

| Example | Ligand | Solvent | Amount of complex (μmol) | Internal pressure (MPa) | Kind/amount of comonomer (μmol) | Polymerization time (sec) | Polymerization temperature (° C.) | Activity Vp (kg/mol/h) | Tm (° C.) | Tc (° C.) | Mw | Mn | Mw/Mn |
|---|---|---|---|---|---|---|---|---|---|---|---|---|---|
| 28 | B-27DM | Toluene (4.2 ml) | 5.0 | 0.3 | 0 | 3600 | 70 | 79 | n/a | n/a | n/a | n/a | n/a |
| 29 | B-27DM | Toluene (4.2 ml) | 5.0 | 0.7 | 0 | 3600 | 70 | 274 | n/a | n/a | n/a | n/a | n/a |

TABLE 5

| Example | Ligand | Solvent | Amount of complex (μmol) | Internal pressure (MPa) | Kind/amount of comonomer (μmol) | Polymerization time (sec) | Polymerization temperature (° C.) | Activity Vp (kg/mol/h) | Tm (° C.) | Tc (° C.) | Mw | Mn | Mw/Mn |
|---|---|---|---|---|---|---|---|---|---|---|---|---|---|
| 30 | B-30 | Toluene (4.2 ml) | 5.0 | 0.3 | 0 | 3600 | 50 | 37 | n/a | n/a | n/a | n/a | n/a |
| 31 | B-30 | Toluene (4.2 ml) | 5.0 | 0.7 | 0 | 3600 | 50 | 54 | n/a | n/a | n/a | n/a | n/a |
| 32 | B-30 | Toluene (4.2 ml) | 5.0 | 0.3 | 0 | 3600 | 70 | 47 | n/a | n/a | n/a | n/a | n/a |
| 33 | B-30 | Toluene (4.2 ml) | 5.0 | 0.7 | 0 | 3600 | 70 | 106 | 128.1 | n/a | 132000 | 29000 | 4.6 |

TABLE 6

| Example | Ligand | Lewis base (amount) | Amount of complex (μmol) | Internal pressure (MPa) | Kind/amount of comonomer (μmol) | Polymerization time (sec) | Polymerization temperature (° C.) | Activity Vp (kg/mol/h) | Tm (° C.) | Tc (° C.) | Mw | Mn | Mw/Mn |
|---|---|---|---|---|---|---|---|---|---|---|---|---|---|
| 34 | B-14 | 2,6-lutidine (1.5 mmol) | 0.20 | 2.8 | 0 | 324 | 70 | 23839 | 128 | 115 | 42500 | 2100 | 20.7 |
| 35 | B-14 | 2,4-lutidine (1.5 μmol) | 0.20 | 2.8 | 0 | 370 | 70 | 18735 | 128 | 115 | 46000 | 2300 | 20.4 |
| 36 | B-14 | 3,5-lutidine (1.5 μmol) | 0.20 | 2.8 | 0 | 1028 | 70 | 3299 | 137 | 112 | 152000 | 56300 | 2.7 |
| 37 | B-14 | furan (1.5 μmol) | 0.20 | 2.8 | 0 | 424 | 70 | 17499 | 129 | 115 | 54500 | 3100 | 17.5 |
| 38 | B-14 | DMAP (1.5 μmol) | 0.20 | 2.8 | 0 | 3601 | 70 | 817 | 136 | 115 | 170000 | 54800 | 3.1 |
| 39 | B-14 | 2,2'-BiPy (1.5 μmol) | 0.20 | 2.8 | 0 | 332 | 70 | 15392 | 128 | 115 | 38000 | 1600 | 24.1 |
| 40 | B-14 | NMI (1.5 μmol) | 0.20 | 2.8 | 0 | 3601 | 70 | 729 | 138 | 112 | 171000 | 59000 | 2.9 |
| 41 | B-14 | pirimidine (1.5 μmol) | 0.20 | 2.8 | 0 | 473 | 70 | 14484 | 129 | 115 | 67000 | 6200 | 10.8 |
| 42 | B-14 | DMAP (2.0 μmol) | 0.80 | 2.8 | tBA (400) | 3602 | 70 | 33 | 106 | 90 | n/a | n/a | n/a |
| 43 | B-14 | DMAP (4.0 μmol) | 0.80 | 2.8 | tBA (400) | 3602 | 70 | 28 | 105 | 87 | 46000 | 27100 | 1.7 |
| 44 | B-14 | DMAP (6.0 μmol) | 0.80 | 2.8 | tBA (400) | 3600 | 70 | 14 | n/a | n/a | n/a | n/a | n/a |
| 45 | B-14 | DMAP (8.0 μmol) | 0.80 | 2.8 | tBA (400) | 3602 | 70 | 21 | n/a | n/a | 43000 | 25300 | 1.7 |
| 46 | B-14 | 2,2'-BiPy (2.0 μmol) | 0.80 | 2.8 | tBA (400) | 3602 | 70 | 14 | n/a | n/a | n/a | n/a | n/a |
| 47 | B-14 | 2,2'-BiPy (4.0 μmol) | 0.80 | 2.8 | tBA (400) | 3601 | 70 | 10 | n/a | n/a | n/a | n/a | n/a |
| 48 | B-14 | 2,2'-BiPy (6.0 μmol) | 0.80 | 2.8 | tBA (400) | 3601 | 70 | 7 | n/a | n/a | n/a | n/a | n/a |
| 49 | B-14 | 2,2'-BiPy (8.0 μmol) | 0.80 | 2.8 | tBA (400) | 3602 | 70 | 5 | n/a | n/a | n/a | n/a | n/a |
| 50 | B-14 | NMI (2.0 μmol) | 0.80 | 2.8 | tBA (400) | 3601 | 70 | 28 | 106 | 87 | 56000 | 35000 | 1.6 |
| 51 | B-14 | NMI (4.0 μmol) | 0.80 | 2.8 | tBA (400) | 3601 | 70 | 25 | 106 | 89 | 57500 | 36000 | 1.6 |
| 52 | B-14 | NMI (6.0 μmol) | 0.80 | 2.8 | tBA (400) | 3602 | 70 | 18 | n/a | n/a | 51500 | 30300 | 1.7 |
| 53 | B-14 | NMI (8.0 μmol) | 0.80 | 2.8 | tBA (400) | 3601 | 70 | 18 | n/a | n/a | 49500 | 31000 | 1.6 |
| 54 | B-14 | pirimidine (2.0 μmol) | 0.80 | 2.8 | tBA (400) | 3600 | 70 | 48 | 105 | 87 | 64500 | 37900 | 1.7 |
| 55 | B-14 | pirimidine (4.0 μmol) | 0.80 | 2.8 | tBA (400) | 3601 | 70 | 50 | 105 | 86 | 62000 | 39000 | 1.6 |
| 56 | B-14 | pirimidine (6.0 μmol) | 0.80 | 2.8 | tBA (400) | 3602 | 70 | 36 | 106 | 88 | 57000 | 35600 | 1.6 |
| 57 | B-14 | pirimidine (8.0 μmol) | 0.80 | 2.8 | tBA (400) | 3600 | 70 | 38 | 105 | 87 | 56000 | 35000 | 1.6 |
| 58 | B-14 | 2,6-lutidine (0.5 μmol) | 0.20 | 2.8 | 0 | 331 | 70 | 21323 | 128 | 115 | 50000 | 2700 | 18.6 |
| 59 | B-14 | 2,4-lutidine (0.5 μmol) | 0.20 | 2.8 | 0 | 371 | 70 | 17626 | 128 | 115 | 55000 | 2600 | 21.1 |
| 60 | B-14 | 3,5-lutidine (0.5 μmol) | 0.20 | 2.8 | 0 | 390 | 70 | 18471 | 129 | 115 | 60500 | 3500 | 17.1 |
| 61 | B-14 | furan (0.5 μmol) | 0.20 | 2.8 | 0 | 403 | 70 | 17004 | 129 | 115 | 59000 | 3500 | 17.1 |
| 62 | B-14 | DMAP (0.5 μmol) | 0.20 | 2.8 | 0 | 3601 | 70 | 794 | 136 | 114 | 173500 | 62000 | 2.8 |
| 63 | B-14 | 2,2'-BiPy (0.5 μmol) | 0.20 | 2.8 | 0 | 338 | 70 | 20492 | 129 | 115 | 53000 | 3100 | 17.1 |
| 64 | B-14 | NMI (0.5 μmol) | 0.20 | 2.8 | 0 | 3602 | 70 | 540 | 136 | 114 | 148000 | 52900 | 2.8 |
| 65 | B-14 | pirimidine (0.5 μmol) | 0.20 | 2.8 | 0 | 409 | 70 | 16596 | 128 | 115 | 52000 | 3000 | 17.4 |

TABLE 7

| Example | Ligand | Solvent | Amount of complex (μmol) | Internal pressure (MPa) | Kind/amount of comonomer (μmol) | Polymerization time (sec) | Polymerization temperature (° C.) | Activity Vp (kg/mol/h) | Tm (° C.) | Tc (° C.) | Mw | Mn | Mw/Mn |
|---|---|---|---|---|---|---|---|---|---|---|---|---|---|
| 66 | B-14 | Toluene (1000 ml) | 10 | 2.8 | 0 | 3600 | 50 | 3050 | 132.8 | 119.2 | 736000 | 368000 | 2.0 |
| 67 | B-14 | Toluene (1000 ml) | 80 | 2.8 | tBA (40.0) | 3600 | 50 | 29 | 119.1 | 108.1 | 297000 | 123800 | 2.4 |
| 68 | B-14 | Toluene (1000 ml) | 82 | 3.0 | tBA (41.0) | 3600 | 50 | 85 | 120.8 | 109.5 | 356000 | 169500 | 2.1 |
| 69 | B-14 | Toluene (1000 ml) | 79 | 3.0 | tBA (20.0) | 3600 | 50 | 163 | 123.0 | 111.6 | 426000 | 193600 | 2.2 |

TABLE 7-continued

| Example | Ligand | Solvent | Amount of complex (μmol) | Internal pressure (MPa) | Kind/amount of comonomer (μmol) | Polymerization time (sec) | Polymerization temperature (°C.) | Activity Vp (kg/mol/h) | Tm (°C.) | Tc (°C.) | Mw | Mn | Mw/Mn |
|---|---|---|---|---|---|---|---|---|---|---|---|---|---|
| 70 | B-14 | Toluene (1000 ml) | 86 | 3.0 | tBA (22.0) | 3600 | 50 | 176 | 123.5 | 111.8 | 444000 | 201800 | 2.2 |
| 71 | B-14 | Toluene (1000 ml) | 160 | 3.0 | tBA (40.0) | 3600 | 50 | 99 | 121.5 | 109.9 | 378000 | 157500 | 2.4 |
| 72 | B-14 | Toluene (1000 ml) | 154 | 3.0 | tBA (19.0) | 3600 | 50 | 198 | 124.1 | 112.0 | 463000 | 210500 | 2.2 |
| 73 | B-14 | Toluene (1000 ml) | 160 | 3.0 | tBA (80.0) | 3600 | 50 | 20 | 112.0 | 98.9 | 107000 | 56300 | 1.9 |
| 74 | B-14 | Toluene (1000 ml) | 161 | 2.0 | tBA (12.4) | 3600 | 70 | 400 | 122.9 | 111.0 | 248000 | 124000 | 2.0 |
| 75 | B-14 | Toluene (1000 ml) | 164 | 2.0 | tBA (27.5) | 3600 | 70 | 95 | 115.5 | 103.1 | 146000 | 76800 | 1.9 |
| 76 | B-14 | Toluene (1000 ml) | 328 | 2.0 | tBA (54.9) | 3600 | 70 | 24 | 107.9 | 94.4 | 73000 | 38400 | 1.9 |
| 77 | B-14 | Toluene (1000 ml) | 172 | 1.0 | tBA (4.1) | 4600 | 70 | 384 | 125.8 | 113.9 | 274000 | 130500 | 2.1 |
| 78 | B-14 | Toluene (1000 ml) | 80 | 3.0 | tBA (20.0) | 3600 | 50 | 106 | 124.3 | 112.2 | 462000 | 220000 | 2.1 |
| 79 | B-14 | Toluene (1000 ml) | 10 | 2.0 | 0 | 1800 | 100 | 19242 | 130.4 | 115.3 | 73000 | 34700 | 2.1 |
| 80 | B-14 | Toluene (1000 ml) | 115 | 2.0 | tBA (12.4) | 1800 | 100 | 158 | 121.4 | 109.4 | 75000 | 39500 | 1.9 |
| 81 | B-14 | Toluene (1000 ml) | 170 | 2.0 | tBA (12.4) | 3600 | 100 | 74 | 121.6 | 109.3 | 73000 | 34800 | 2.1 |
| 82 | B-14 | Toluene (1000 ml) | 170 | 2.0 | tBA (12.4) | 3600 | 90 | 650 | 125.9 | 112.4 | 114000 | 54300 | 2.1 |
| 83 | B-14 | Toluene (1000 ml) | 163 | 2.0 | tBA (12.4) | 1800 | 80 | 645 | 122.5 | 110.5 | 148000 | 82200 | 1.8 |
| 84 | B-14 | Toluene (1000 ml) | 331 | 2.0 | tBA (54.9) | 3600 | 70 | 99 | 108.4 | 92.8 | 97000 | 51100 | 1.9 |
| 85 | B-30 | Toluene (1000 ml) | 10 | 3.0 | 0 | 612 | 70 | 31938 | 135.9 | 114.6 | 451000 | 150300 | 3.0 |
| 86 | B-30 | Toluene (1000 ml) | 80 | 3.0 | tBA (41.0) | 3600 | 70 | 89 | 111.9 | 97.1 | 109000 | 54500 | 2.0 |
| 87 | B-30 | Toluene (1000 ml) | 80 | 3.0 | tBA (41.0) | 3600 | 70 | 73 | 111.9 | 98.3 | 107000 | 56300 | 1.9 |

TABLE 8

| Example | Ligand | Solvent | Amount of complex (μmol) | Internal pressure (MPa) | Kind/amount of comonomer (μmol) | Polymerization time (sec) | Polymerization temperature (°C.) | Activity Vp (kg/mol/h) | Tm (°C.) | Tc (°C.) | Mw | Mn | Mw/Mn |
|---|---|---|---|---|---|---|---|---|---|---|---|---|---|
| 88 | B-56DM | Toluene (4.2 ml) | 5.0 | 0.3 | 0 | 3600 | 50 | 58 | n/a | n/a | n/a | n/a | n/a |
| 89 | B-56DM | Toluene (4.2 ml) | 5.0 | 0.7 | 0 | 3600 | 50 | 106 | n/a | n/a | n/a | n/a | n/a |
| 90 | B-56DM | Toluene (4.2 ml) | 5.0 | 0.3 | 0 | 1500 | 70 | 460 | n/a | n/a | n/a | n/a | n/a |
| 91 | B-56DM | Toluene (4.2 ml) | 5.0 | 0.5 | 0 | 1200 | 70 | 911 | n/a | n/a | n/a | n/a | n/a |

INDUSTRIAL APPLICATION

According to the present invention, production of a copolymer of (meth)acrylate and α-olefin which are industrially easily available becomes possible and molecular weight of the resultant polymer is high. Not only the copolymer, but also an α-olefin homopolymer can have a high molecular weight. Generally, molecular weight is one of dominant factors in physical properties of polymer, and interaction between polymer chains is strengthened by increasing molecular weight, therefore, the polymer or copolymer obtained by the present invention is superior in mechanical and thermal properties, and applicable as a useful molded product. Furthermore, in the present invention, a catalyst using nickel as a metal center instead of rare and precious palladium can be used. Thus, the present invention provides a novel method for producing such α-olefin polymer and α-olefin/(meth)acrylate copolymer, and is industrially extremely useful.

The invention claimed is:

1. A metal complex represented by formula (D):

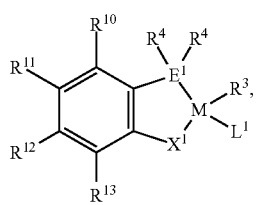

(D)

wherein:
M represents Ni or Pd;
$R^3$ represents hydrogen or a hydrocarbon group having 1 to 20 carbon atoms and optionally containing a heteroatom;
$L^1$ represents a ligand coordinated to M;
$R^3$ and $L^1$ optionally bind each other to form a ring;
$X^1$ represents oxygen or sulfur;
$E^1$ represents phosphorus, arsenic or antimony;
$R^4$ each independently represents hydrogen or a hydrocarbon group having 1 to 20 carbon atoms and optionally containing a heteroatom, wherein at least one of $R^4$ is a hydrocarbon group having two or more heteroatom-containing groups;
$R^{10}$, $R^{11}$, and $R^{12}$ each independently represent hydrogen, a halogen, a hydrocarbon group having 1 to 30 carbon atoms and optionally containing a heteroatom, $OR^2$, $CO_2R^2$, $CO_2M'$, $C(O)N(R^1)_2$, $C(O)R^2$, $SR^2$, $SO_2R^2$, $SOR^2$, $OSO_2R^2$, $P(O)(OR^2)_{2-y}(R^1)_y$, $CN$, $NHR^2$, $N(R^2)_2$, $Si(OR^1)_{3-x}(R^1)_x$, $OSi(OR^1)_{3-x}(R^1)_x$, $NO_2$, $SO_3M'$, $PO_3M'_2$, $P(O)(OR^2)_2M'$ or an epoxy containing group;
$R^{13}$ represents a hydrocarbon group having 1 to 30 carbon atoms and optionally containing a heteroatom;
$R^1$ represents hydrogen or a hydrocarbon group having 1 to 20 carbon atoms;
$R^2$ represents a hydrocarbon group having 1 to 20 carbon atoms;
M' represents an alkali metal, an alkaline earth metal, ammonium, quaternary ammonium or phosphonium;
x represents an integer of 0 to 3; and
y represents an integer of 0 to 2,
such that a plurality of groups selected from the group consisting of $R^4$, $R^{10}$, $R^{11}$, and $R^{12}$ optionally bind each other to form an aliphatic ring, an aromatic ring, or a hetero ring containing a heteroatom selected from the group consisting of oxygen, nitrogen and sulfur, said rings being an optionally-substituted 5 to 8 membered ring.

2. The metal complex according to claim 1, wherein M is Ni.

3. The metal complex according to claim 1, wherein M is Pd.

4. A method for producing the metal complex according to claim 1, the method comprising contacting a compound represented by formula (A) or (B) with a transition metal complex (C) comprising Ni or Pd:

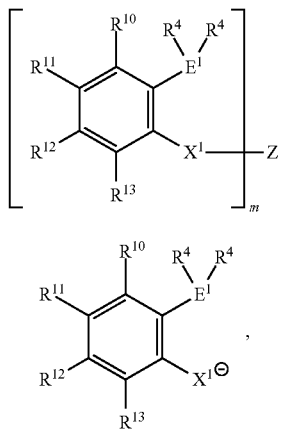

wherein:

Z represents a hydrogen or an elimination group;

represents a valence of Z; and $X^1, E^1, R^4, R^{10}, R^{11}, R^{12}$ and $R^{13}$ are as previously defined.

5. A method for producing an α-olefin polymer, the method comprising polymerizing an α-olefin in the presence of the metal complex according to claim 1.

6. The method according to claim 5, wherein the polymerizing occurs in the presence of a Lewis base.

7. The method according to claim 5, wherein the polymerizing occurs in the absence of an organic aluminium compound.

8. A method for producing an α-olefin/(meth)acrylate copolymer, the method comprising copolymerizing (a) an α-olefin and (b) a (meth)acrylate in the presence of the metal complex according to claim 1.

9. The method according to claim 8, wherein the copolymerizing occurs in the presence of Lewis base.

10. The method for according to claim 8, wherein the copolymerizing occurs in the absence of organic aluminium compound.

* * * * *